United States Patent
Fisher et al.

(10) Patent No.: US 10,254,290 B2
(45) Date of Patent: Apr. 9, 2019

(54) SYSTEMS AND METHODS FOR IDENTIFYING PROTEIN STABILIZERS

(71) Applicant: The University of Kansas, Lawrence, KS (US)

(72) Inventors: Mark T. Fisher, Prairie Village, KS (US); Subhashchandra Naik, Kansas City, KS (US)

(73) Assignee: The University of Kansas, Lawrence, KS (US)

( * ) Notice: Subject to any disclaimer, the term of this patent is extended or adjusted under 35 U.S.C. 154(b) by 25 days.

(21) Appl. No.: 15/450,716

(22) Filed: Mar. 6, 2017

(65) Prior Publication Data

US 2017/0176450 A1 Jun. 22, 2017

Related U.S. Application Data

(62) Division of application No. 14/381,375, filed as application No. PCT/US2013/027822 on Feb. 26, 2013.

(Continued)

(51) Int. Cl.
*G01N 33/68* (2006.01)
*G01N 33/543* (2006.01)
(Continued)

(52) U.S. Cl.
CPC ....... *G01N 33/6845* (2013.01); *G01N 21/658* (2013.01); *G01N 33/54373* (2013.01);
(Continued)

(58) Field of Classification Search
CPC ............. G01N 33/6845; G01N 21/658; G01N 33/54373; C12Q 1/32
See application file for complete search history.

(56) References Cited

U.S. PATENT DOCUMENTS 5,585,277 A 12/1996 Bowie et al.
6,887,682 B2 5/2005 Fisher et al.
(Continued)

OTHER PUBLICATIONS

Naik, S. et al. "Identifying Protein Stabilizing Ligands Using GroEL", Biopolymers, Mar. 2010, 93(3), pp. 237-251. doi: 10.1002/bip.21319.

(Continued)

*Primary Examiner* — Melanie Brown
(74) *Attorney, Agent, or Firm* — Maschoff Brennan

(57) ABSTRACT

A device for studying protein conformation transformation can include a macroscopic substrate, and chaperonin proteins bound to the substrate, each chaperonin protein being capable of binding to a protein of interest during or after undergoing protein conformation transformation. The device may also include the proteins of interest bound to the substrate, where the substrate is included in a label-free assay system. A method of studying protein conformation transformation can include: providing a macroscopic substrate bound with the chaperonin protein and immersing the chaperonin protein in a study composition having the protein of interest, or include providing a macroscopic substrate bound with the protein of interest; and immersing the protein in a study composition having the chaperonin. Such a method can be done with and without a potential stabilizer in order to determine whether the potential stabilizer stabilizes the protein of interest.

22 Claims, 15 Drawing Sheets

Related U.S. Application Data

(60) Provisional application No. 61/603,584, filed on Feb. 27, 2012.

(51) Int. Cl.
   *G01N 21/65* (2006.01)
   *C12Q 1/32* (2006.01)

(52) U.S. Cl.
   CPC ..... *C12Q 1/32* (2013.01); *G01N 2333/90666* (2013.01); *G01N 2333/954* (2013.01); *G01N 2500/00* (2013.01); *G01N 2500/04* (2013.01); *G01N 2500/20* (2013.01)

(56) References Cited

U.S. PATENT DOCUMENTS

| | | | |
|---|---|---|---|
| 2002/0001815 A1 | 1/2002 | Hindsgaul et al. | |
| 2003/0082827 A1 | 5/2003 | Craig et al. | |
| 2003/0180718 A1* | 9/2003 | Pillutla | C12N 15/1037 506/7 |
| 2005/0196824 A1 | 9/2005 | Fisher et al. | |
| 2007/0059794 A1 | 3/2007 | Ideno et al. | |
| 2009/0093061 A1 | 4/2009 | Tsai et al. | |
| 2010/0099203 A1 | 4/2010 | Chang et al. | |
| 2011/0053795 A1 | 3/2011 | Fisher et al. | |
| 2012/0021416 A1 | 1/2012 | Zassenhaus | |

OTHER PUBLICATIONS

Rothbard, J. B., et al., "Chaperone Activity of a B-Crystallin Is Responsible for Its Incorrect Assignment as an Autoantigen in Multiple Sclerosis", The Journal of Immunology, Feb. 25, 2011, vol. 186, pp. 4263-4268. doi: 10.1049/jimmunol.1003934.

Katayama et al., "GroEL as a molecular scaffold for structural analysas of the antrax toxin pore", Jun. 22, 2008, Nature Structural & Molecular Biology, vol. 15, No. 7, pp. 754-760. doi: 10.1038/nsmb.1442.

Sota et al., "Detection of Conformational Changes in an Immobilized Protein Using Surface Plasmon Resonance", Analytical Chemistry, 1998, vol. 70, pp. 2019-2024.

Correia et al. (Oct. 20, 2014). Probing the Kinetic Stabilities of Friedreich's Ataxia Clinical Variants Using a Solid Phase GroEL Chaperonin Capture Platform. Biomolecules, 4, 956-979. doi:10.3390/biom4040956.

Naik et al. (Aug. 21, 2013). Monitoring the Kinetics of the pH-Driven Transition of the Anthrax Toxin Prepore to the Pore by Biolayer Interferometry and Surface Plasmon Resonance. Biomolecules, 52, 63335-6347. doi:10.1021/bi400705n.

Naik et al. (Jul. 14, 2014). Probing structurally altered and aggregated states of therapeutically relevant proteins using GroEL coupled to bio-layer interferometry. Protein Science, 23, 1461-1478. doi:10.1002/pro.2515.

Lea et al. (Mar. 30, 2016). Chaperonin-based biolayer interferometry to assess the kinetic stability of metastable, aggregation-prone proteins. Manuscript submitted for publication. Manuscript id:bi-2016-00293t.

* cited by examiner

SYSTEMS AND METHODS FOR IDENTIFYING PROTEIN STABILIZERS

CROSS-REFERENCE TO RELATED APPLICATIONS

This patent application is a divisional application of U.S. application Ser. No. 14/381,375 filed Aug. 27, 2014, which is a nationalization of PCT/US2013/027822 filed Feb. 26, 2013, which claims the benefit of U.S. Provisional Application No. 61/603,584 filed Feb. 27, 2012, which applications are incorporated herein by specific reference in their entirety.

STATEMENT OF GOVERNMENT SUPPORT

This invention was made with Government support under Grant No. R01AI090085-01 awarded by the National Institutes of Health. The Government has certain rights in this invention

BACKGROUND

Numerous classes of bacteria and virus particles include proteins that undergo transitions from soluble to membrane inserted forms, which can severely compromise a human cell and the human organism in general. Often, the change in protein conformation from water soluble to membrane inserted (e.g., membrane soluble) occurs by the protein opening to expose hydrophobic motifs (e.g., amino acids, peptides, or polypeptides) that are usually within the protein core. The change in protein conformation from water soluble to membrane inserted configurations can occur during acidification, such as occurs in an endosome or lysosome. As such, inhibiting the change in protein conformation from water soluble to membrane inserted may be useful for inhibiting the negative consequences, such as disease or compromised health, which may arise from such a change in protein conformation.

Currently, some high-throughput technologies that are used to identify small molecule protein stabilizers rely on processes that heat and denature the target protein that may change conformation. Unfortunately, heating and denaturing proteins may be prone to artifacts ranging from heat induced aggregation and non-equilibrium transitions (i.e., dye influence equilibrium). Also, such heating and denaturing techniques are not suitable for many proteins. One of the most problematic issues with current techniques includes the potential ligands being identified under non-physiological temperatures. No high throughput systems exist where the screens to identify protein stabilizers are performed under physiological or near physiological conditions. Furthermore, current techniques include non-equilibrium processes and destroy the target protein. The identified ligands must bind to the protein under non-physiological conditions and these physical constraints often results in false positive and negative results.

One approach to inhibit such protein conformation transformations can include preventing an acid dependent transition, which may be accomplished using general or more specific protein stabilizers. Therefore, there is a need in the art for methods for identifying and testing protein stabilizers that can inhibit protein conformation transformations, such as those that occur with bacterial toxins and viral particle proteins.

BRIEF DESCRIPTION OF FIGURES

The information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
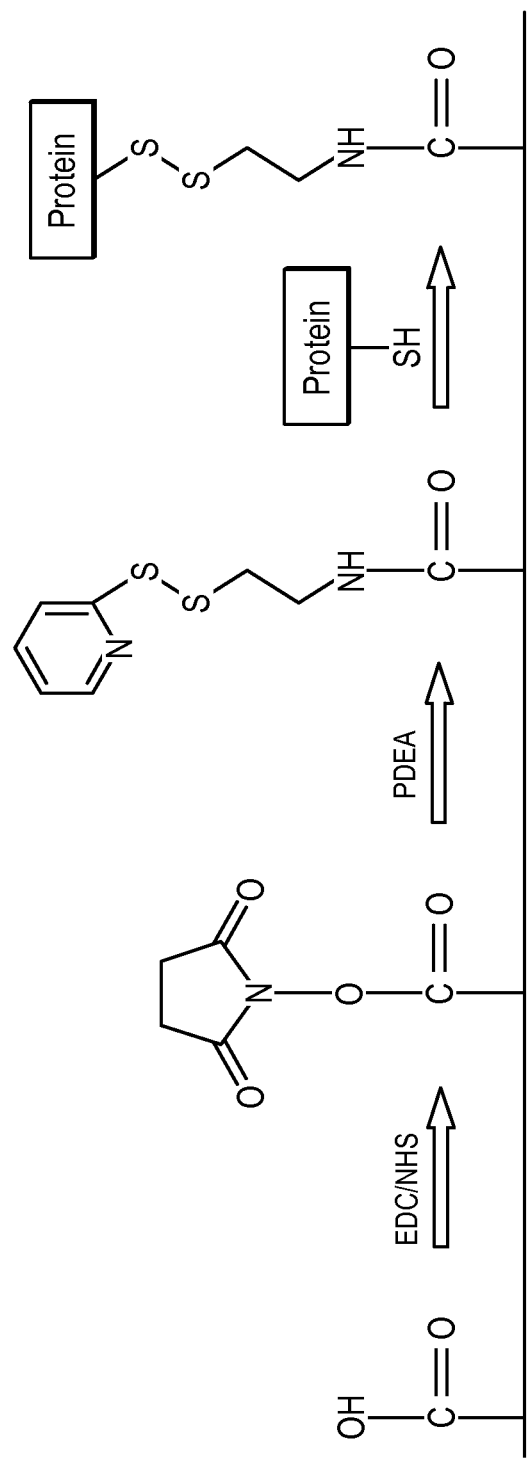
FIG. 1 illustrates an embodiment of a reaction scheme for linking a protein to a substrate.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes devices, systems, and methods for identifying or studying substances that can inhibit protein conformation transformations. This can include identifying substances that inhibit bacterial protein conformation transformation from a benign conformation to a toxic conformation or any other conformation transformation. This can also specifically include identifying substances that inhibit bacterial or viral proteins from transforming from a non-membrane insertable conformation to a membrane insertable conformation. In one aspect, the invention can include methodologies involving protein confirmation studies or screenings for protein stabilizers that inhibit protein conformation transformations, which methodologies can be conducted with systems and label-free methods such as high throughput biolayer interferometry (BLI), surface plasmon resonance (SPR) detection adapted and coupled with high-throughput screening systems. The techniques described herein can also be used with other technologies to screen for protein stabilizers. However, the devices, systems, and methods can also be used to identify potential protein destabilizers that promote or induce a conformation transformation.

While it is well known that proteins can undergo conformation transformations in highly ionic compositions or at high temperatures, the present invention contemplates protein conformation transformations at physiological conditions, such as those found within a human subject or other animal. That is, the protein conformation transformation described herein in many embodiments is different from denaturation. However, denaturation can be useful in some embodiments. One aspect can include using a denaturing boost to speed up kinetics of a conformation transformation. In one aspect, the protein conformation transformation described herein specifically does not include complete denaturation. However, an embodiment of the invention affirmatively uses denaturation to enhance kinetics, where the denaturant is washed from the target protein before the target protein interacts with a chaperonin for binding studies (see FIGS. 11-13).

The invention can include identifying protein stabilizers that inhibit protein conformation transformations. Such protein stabilizers can be useful for preventing, inhibiting, and treating diseases or disease conditions associated or occur in part from protein conformation transformations. As such, the present invention can be used for identifying compounds or substances that can be used as protein stabilizers that stabilize either a wide variety of proteins or that are specific in stabilizing a particular protein that has a protein conformation transformation associated with toxicity or disease state in a host subject. The protein stabilizers may inhibit conformation change and inhibit aggregation of the protein that may arise from the conformation transformation. The present invention can identify protein stabilizers that stabilize one or more proteins (e.g., bacterial toxins) at one or more pH values or over a range of pH values, such as pH values that cover cytoplasmic, serum, endosome, and lysosome pH environments.

In one embodiment, the present invention can include a method of coupling a protein to a substrate. The substrate can be a BLI probe or SPR well or any other suitable substrate to be exposed to a composition. The substrate can be coupled to various types of proteins described herein, such as capture proteins, target proteins, chaperonins, antibodies, or others. The substrate can be coupled to polypeptides or recombinant proteins through sulfhyryl linkages as per FIG. 1 described below or other suitable coupling.

FIG. 1 shows an attachment scheme that can be used for a protein (e.g., capture protein, target protein, chaperonin, antibody, etc.) to be bound and immobilized onto a substrate (e.g., BLI or SPR substrate) surface via thiol coupling with specific orientation, which attachment is through a sulfhydryl group. Particularly, FIG. 1 shows the attachment scheme with a capture protein (e.g., lethal factor, LFN) protein through thiol coupling. The thiol coupling can include an active disulfide moiety introduced either on the dextran matrix or on the ligand molecule. 2-(2-pyrdinyldithio) ethaneamine (PDEA) can be used to introduce the di-sulfide group for attachment exchange. Here, the LFN protein can be considered a capture protein because it interacts with an anthrax protein that has a prepore and pore conformation so that the LFN can capture this protein for the purposes of the invention. Other types of proteins that interact or bind with other proteins can also be used as capture proteins. The coupling can also be applied to the prepore and pore conformations as well as other types of conformation transforming proteins.

In one embodiment, the present invention can include a label-free system and method that uses a capture protein (e.g., LFN) coupled to a substrate directly or through a linker. The capture protein can bind with a target protein, where the target protein can be in a first conformation and can transform into a second conformation. Often, the first conformation of the target protein is benign or relatively non-toxic (e.g., anthrax prepore conformation), but the second conformation (e.g., anthrax pore conformation) is toxic or lethal, either directly or indirectly. For example, the pore conformation can be lethal by forming a pore in an endosome and allowing toxic substances (e.g. anthrax components LFN or EF) to transit into the cytoplasm. That is, the prepore conformation can transform into a pore conformation where the pore conformation itself is not toxic but it destabilizes or inserts into an endosomal membrane wall to form a pore therein and to allow toxins to flow through the membrane and into the cytoplasm of a cell. The target protein can be the protein of interest that is tested to determine whether or not a potential stabilizing substance can inhibit the target protein from transforming from a first conformation (e.g., benign) to a second conformation (e.g., toxic). The target protein can also be tested to determine a substance that inhibits the target protein in one of its conformations from binding with a capture protein or inhibit other aggregations. Often, a substance inhibiting the transformation from a first conformation to a second conformation can result in the substance being a drug candidate, especially when the second conformation is toxic or results in a disease state.

Figure 2:
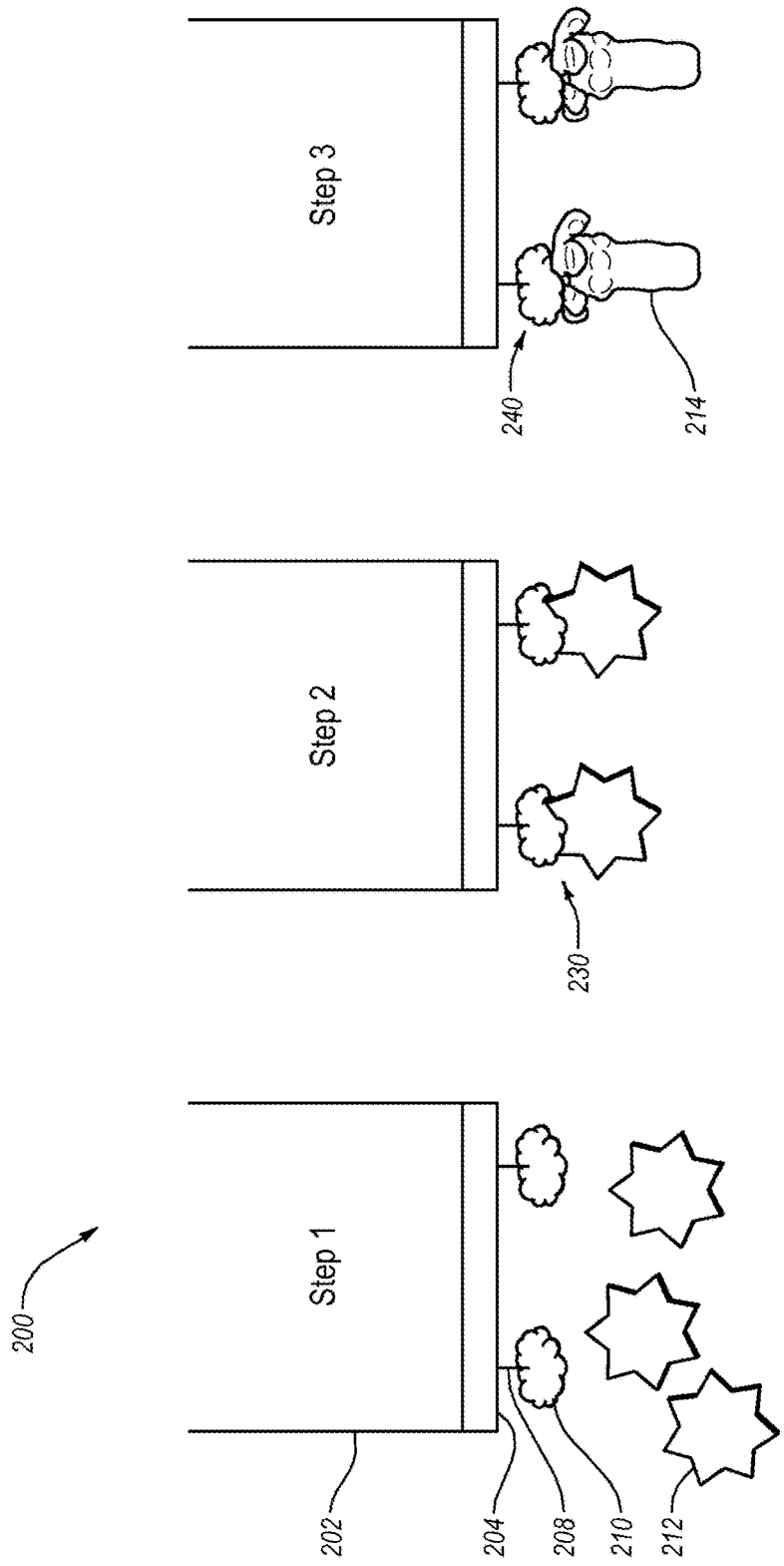
FIG. 2 illustrates an embodiment of a system and method for inducing a target protein linked to a substrate to change conformation.

FIG. 2 illustrates the process 200 for following the target protein unfolding and refolding transitions. Here, the example given is the anthrax toxin prepore (e.g., smaller size) to pore transition (e.g., larger size). For SPR a flow of solution having the prepore over the SPR substrate having the LFN bound thereto through a sulfhydryl linkage is used. For BLI, a BLI tip having the LFN bound thereto is dipped into a solution having the anthrax prepore. In both instances, the LFN associates with the prepore, and a pH change causes the prepore to transform to the pore. As shown, a substrate 202 includes a surface 204 that has a linker 208 having one end coupled thereto and another end coupled to a capture protein 210. In Step 1, the substrate 202 having the capture protein 210 is introduced to a solution having a target protein in a first conformation 212, which is considered to be a prepore in an anthrax example. Step 2 shows the capture protein 210 associating with the target protein in the first conformation 212. Step 3 involves a change in pH (e.g., endososmal pH change) until the target protein in the first conformation 212 changes to a second conformation 214. Here, the second conformation 214 is toxic or leads to a disease state.

In view of FIG. 2, Step 1 of SPR includes the flow of the anthrax prepore (e.g., 212) over the LFN (e.g., 210) immobilized on the SPR surface (e.g., 204). Step 2 of SPR includes the anthrax prepore 212 associating with the LFN 210 attached to the SPR surface 204. The LFN 210 and prepore 212 form complex 230. Then, there is a change of buffer to pH 5-6.5 to induce the anthrax prepore 212 to pore 214 conversion (induced by pH change). Step 3 of SPR includes the anthrax pore 214 associated with the LFN 210, and monitoring conformational change via changes in protein thickness and/or refractive index during the conformational transition. The LFN 210 and pore 214 form complex 240. Step 1 of BLI includes the immobilized LFN 210 via sulfhydryl linkage onto a BLI tip surface (e.g., 210) that is dipped into a solution having the anthrax prepore 212. Step 2 includes the anthrax prepore 212 associating in an orientation dependent manner with the LFN 210 that is on the BLI tip surface 204 to form complex 230. Step 3 of BLI includes immersion of the BLI tip surface 204 having the prepore 212 associated with LFN 210 from neutral pH (pH 7.5-7) to endosomal acidic pH values (pH 6.5 to 5.0) to induce transition from prepore 212 to pore 214 and formation of complex 240 that is detected by BLI techniques.

In one embodiment, the conformational transformations described herein can involve partial unfolding (e.g., incomplete unfolding) alone or partial unfolding followed by refolding. Bacterial toxin transitions, such as those following the pH dependent unfolding and refolding of the anthrax toxin pore transformation, can be readily observed using either BLI or SPR. SPR results (not shown) of an anthrax prepore conformational transition to pore changes at pH 6.5, where the data obtained with a flow rate of 5 µL/min allowed formation of the LFN/prepore complex at pH 7.5, when the buffer changed to 6.5, the LFN/pore complex formed (e.g., transition from first conformation to second conformation) to give a measurable signal, and when returned to pH 7.5 the LFN/pore complex persisted.

BLI studies also detected the anthrax prepore to pore transition. Here, LFN was immobilized on the probe surface using EDC/NHS/PDEA, and then the prepore was bound to LFN at pH 7.5. The conformation change followed by changing the pH of buffer to 7, 6.75 and 6.5 (all duplicate samples.). No transition occurred at pH 7.4. After forming, the LFN/pore complex persisted after a return to pH 7.5. This indicated that the signals of the transitions depend on the pH.

Figure 3:
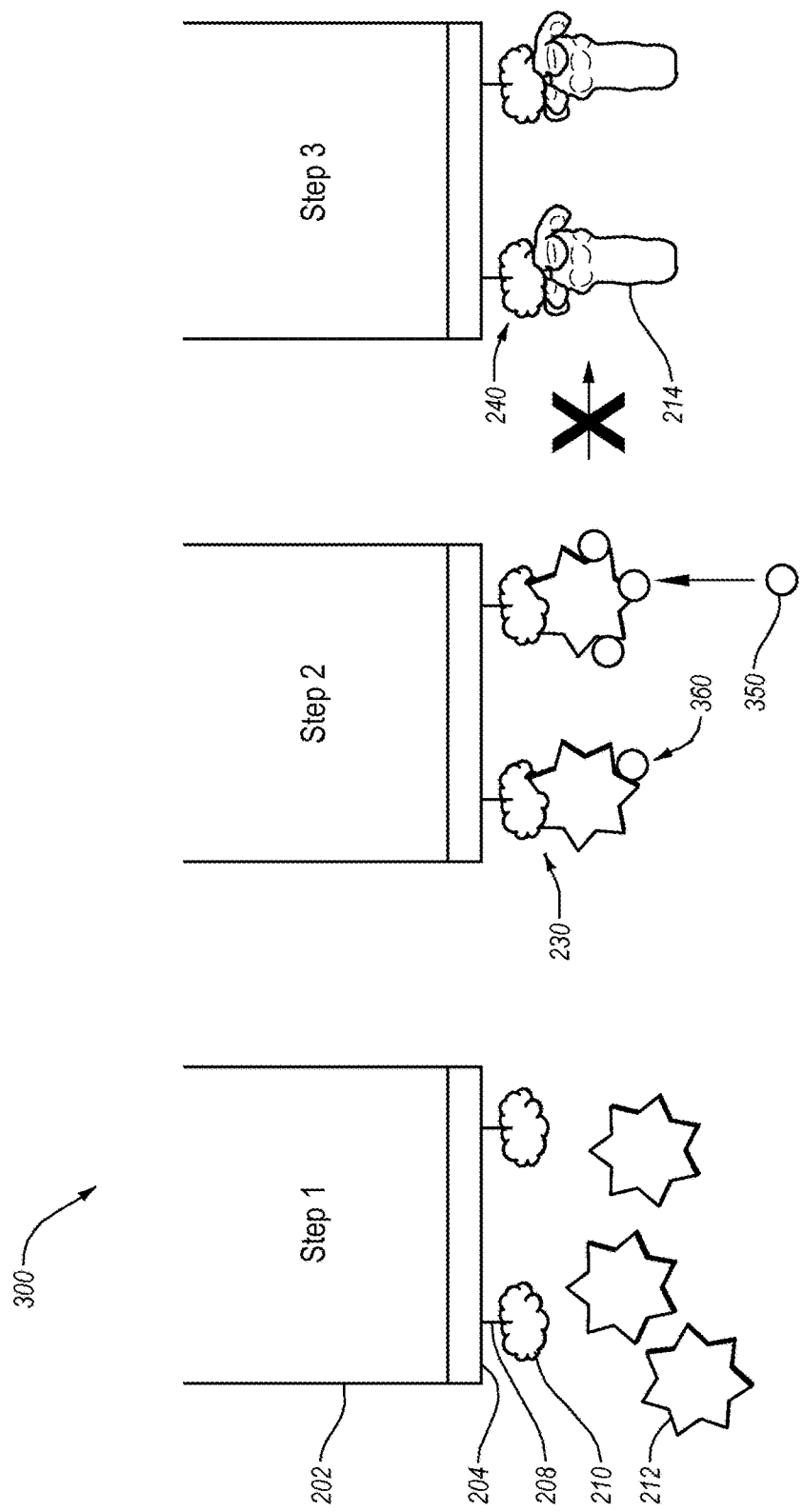
FIG. 3 illustrates an embodiment of a system and method for screening a substance for inhibiting a target protein linked to a substrate from changing conformation.
Figure 4:
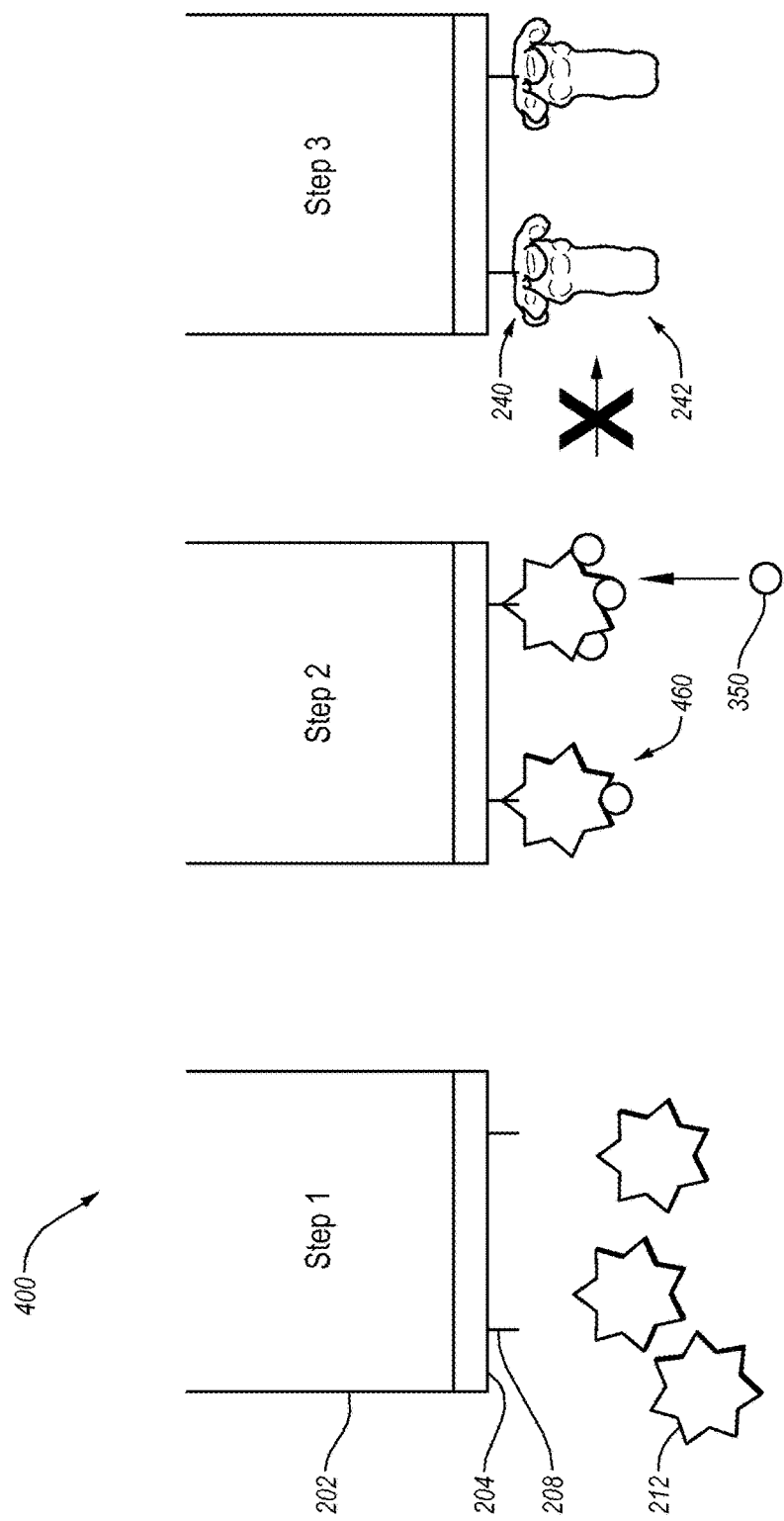
FIG. 4 illustrates an embodiment of a system and method for screening a substance for inhibiting a target protein linked to a substrate from changing conformation.

In one embodiment, the process can be used to identify protein stabilizers that actually inhibit the initial protein conformation transformation process (i.e., preaggregation states) rather than merely inhibit aggregation of proteins that have already undergone a transformation. The readout of the inhibition would be either an abolishment or significant decrease in the kinetics of transition of the anthrax toxin attached through two different protocols (see FIGS. 3 and 4 for BLI examples, discussed below). FIGS. 3 and 4 show two different attachment screens to emphasize the various ways that can be used to immobilize the proteins, which can be capture, target, or chaperonin or other. While the anthrax prepore toxin is used as an example, the present invention applies to any protein that changes from one conformation to another conformation upon a stimulus. The substances that inhibit the conformational changes can be identified for general inhibition of conformational changes or for specific inhibition of specific protein conformational changes that involve partial unfolding or exposure of hydrophobic surfaces. All protein conformational change can be probed using the invention described herein.

FIG. 3 shows a process 300 of using a stabilizer substance 350 in order to stabilize a protein and inhibiting conformational changes. The same components of FIG. 2 are used herein in addition to a potential stabilizer substance 350 (e.g., stabilizer). Here, the "X" between Step 2 and Step 3 shows that the protein cannot change from the prepore conformation 212 to the pore conformation 214. The stabilizer 350 can be any substance, but often can be a small molecule according to common medicines or can be a protein or other substance (e.g., antibodies, proteins, polypeptide, polynucleotides, nucleic acids, polymers, macromolecules, or the like). The stabilizer 350 can be a prophylactic that inhibits the conformational change and thereby inhibits the disease state associated with the conformational change. Step 1 of FIG. 3 shows the anthrax prepore conformation 212 protein being presented to a BLI surface 204 having the LFN protein 210 bound thereto via sulfhydryl linkage 208. Step 2 of FIG. 3 shows a stabilizer 350 binding with the anthrax prepore 212, where one prepore 212 binds one stabilizer 350 and another prepore 212 binds three stabilizers 350. Any number of one or more stabilizers 350 may bond or otherwise associate with the prepore 212 to inhibit the conformational change to the pore 214. Step 3 of FIG. 3 is not reached as shown by the "X" because the stabilizers 350 inhibit the conformational change from prepore 212 to pore 214. The protocol to attempt to induce conformational change from prepore 212 to pore 214 conformation includes removing the BLI tip from pH 7.4 and dipping the tip into a solution having pH 7.4 to 6.5 and attempting to detect conversion induced by pH change. Step 3 is monitored by monitoring and/or measuring the protein thickness increase and/or difference in reflected light.

FIG. 4 shows a process 400 where a protein can be immobilized directly to a substrate surface 204, such as SPR and BLI (shown), for testing whether or not a substance can inhibit the conformational change of a protein from one conformation 212 to another conformation 214. The example shows immobilized the prepore 212 directly on the BLI substrate surface 204 to examine inhibition of conformational change of the prepore 212 in the presence of a stabilizer 350. Here, change in conformation from prepore 212 to pore 214 can be identified via protein thickness analysis. Step 1 of FIG. 4 shows the anthrax prepore 212 being bound directly to the BLI surface 204 without the LFN protein 210 via specific sulfhydryl linkage 208 on Domain 1 to orient the prepore 212 (e.g., soluble form) so that any conformational change allows the transition to pore 214 to occur away from the BLI surface 204. The anthrax prepore 212 can be bound to the BLI surface 204 using the chemistry of FIG. 1. Step 2 of FIG. 4 shows the stabilizer 350 presented to and binding with the prepore 212. Step 3 of FIG. 4 involves attempting to conformationally change the prepore 212 to the pore 214; however, the "X" shows the conformational transition is inhibited by the stabilizer 350. Step 3 includes removing the BLI tip from pH 7.4 and dipping the BLI tip into a solution having pH from 7.4 to 6.5, such as recited in connection with Step 3 of FIG. 3. As such, FIG. 4 shows the assays to determine stabilizers of proteins that inhibit the protein from conformational translation can be identified as potential prophylactic agents (e.g., new anti-bacterial compounds).

In one embodiment, the present invention can include a label-free system to identify protein stabilizers that stabilize target proteins at physiological or near physiological conditions using a chaperonin platform. The present invention can include a label-free high throughput screening method to examine the stability of target proteins by screening small molecule libraries or any other potential substance that inhibits target protein transformation under near physiological conditions using a chaperonin (e.g., GroEL chaperonin) that will bind to the target protein as a dynamic detection system. The basis for the invention takes advantage of the inherent dynamic folding/unfolding equilibrium that exists for all proteins. The chaperonin can bind particular target proteins as they transiently expose hydrophobic surfaces from their partially folded forms. The partitioning kinetics can be followed using the BLI high throughput system (Fortebio Octet™) or SPR or other suitable technology. With BLI as an example, the chaperonin can be attached to the BLI tip substrate to dip into a target protein solution. Alternatively, the capture protein and/or target protein can be attached to the BLI tip substrate to dip into a chaperonin solution. The chaperonin will bind with transitioned target proteins (e.g., second conformation), but has no or low binding with folded target proteins (e.g., first conformation). Stated another way, the chaperonin will not bind (or have low binding) to a protein in a first conformation, but will bind to the protein (or have significantly increased binding) when in a second conformation. Potential protein stabilizers can be screened to see which ones inhibit the chaperonin from binding to the target protein by the stabilizer retaining the protein in the first conformation. In the presence of a potential protein stabilizer, the partitioning kinetic amplitudes show significant declines (e.g., inhibition of partitioning) or even abolish global partitioning, which is scored as a potential lead compound. Once identified, potential protein stabilizer compounds can be further tested with target proteins in secondary screens. To eliminate the possibility of the compound inhibiting the direct chaperonin interaction, the folding functionality of the chaperonin can be tested using a protein binding/folding assay with monomeric dihydrofolate reductase (DHFR).

While the present invention is applicable to stabilizers of bacterial toxin and viral particle transitions, it may also be used for identifying any type of stabilizer of protein conformation transformations, which may include stabilizers of slowly transitioning proteins such as prions as well as slowly dissociating oligomeric proteins such as the multi-mer of a protein (e.g., where dissociation of the monomer followed by the aggregation appears to be the causal element resulting in many diseases, such as Parkinson's) and the like.

Figure 5:
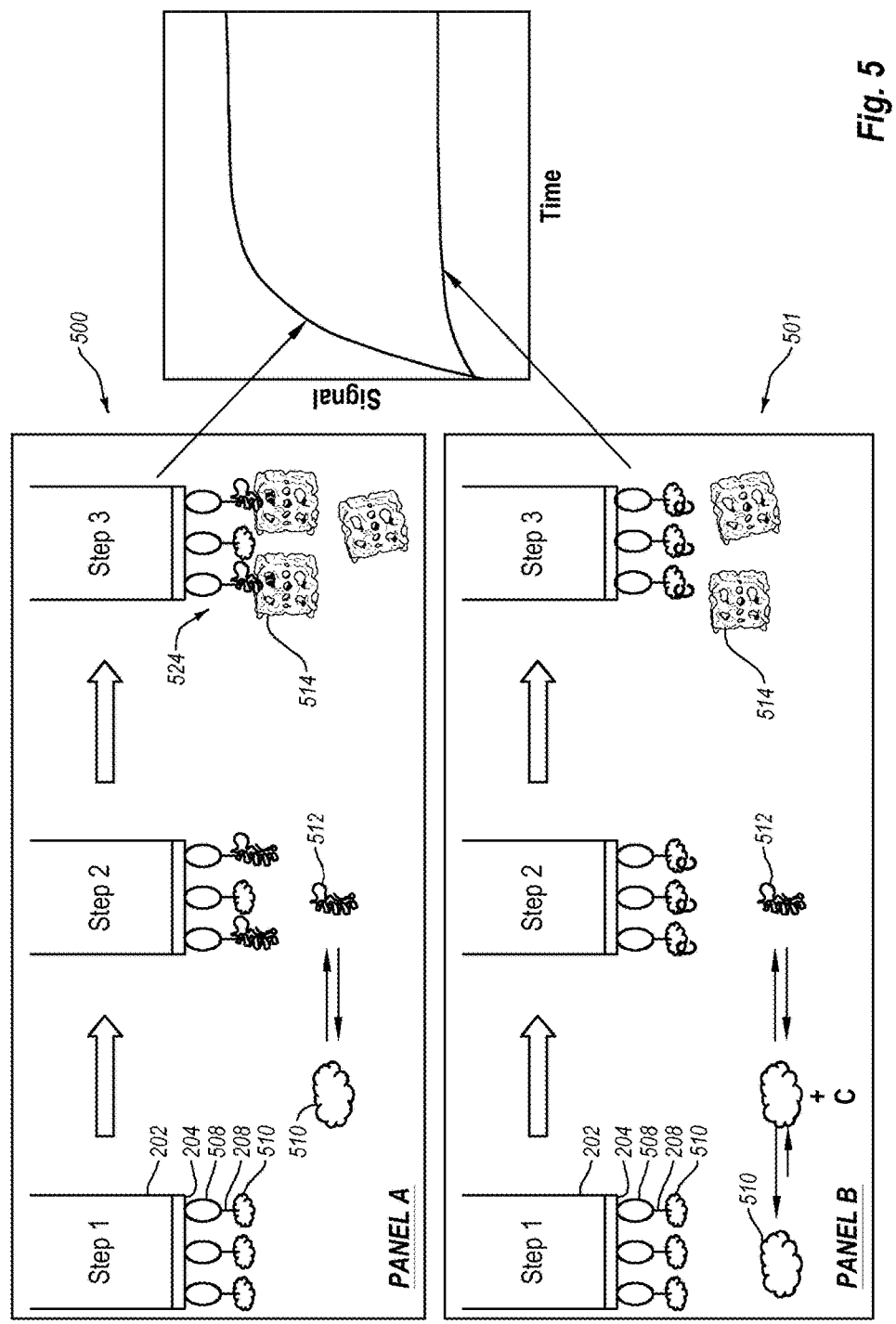
FIG. 5 illustrates an embodiment of a system and method for screening a substance for inhibiting a target protein linked to a substrate from changing conformation and associating with a chaperonin.

FIG. 5 provides a process 500 for using a chaperonin 514 in solution to detect a transitioned protein 512 that is immobilized on a surface 204 of a substrate 202. The protein can go from folded conformation 510 to transitioned conformation 512. The protein in either conformation can be immobilized directly or through a linker 508 to the surface 204 of the substrate 202. For example, the linker 208 can be a spacer, such as a stable chimeric protein that is inert to chaperonin binding, where the chaperonin can be GroEL. As shown in Step 1 of Panel A of FIG. 5, the BLI tip surface 204 couples to one end of a spacer 508 with the other end of the spacer 508 coupled to a protein in a first conformation 510 (e.g., folded). In Step 2 of Panel 1, the protein can then be subjected to conditions (e.g., pH change or other natural unfolding transitions) that cause conformational change to a second conformation 512 (e.g., transitioned). It should be noted that not all of the proteins need to change or will change conformation, where one protein is shown to not change conformation. Step 3 of Panel A shows the second conformation 512 of the protein being introduced to a chaperonin 512 and can bind with the chaperonin 514 of the protein, where the protein in the first conformation 510 does not bind with the chaperonin 514. The transitioned protein 512 and chaperonin form complex 524. Panel B is substantially similar to Panel A except a stabilizer (e.g., corrector or "C") is introduced into the protein in the first conformation in either Step 1 or Step 2 before pH change. As such, the stabilizer C inhibits the protein in the first conformation 510 to change to the second conformation 512, and thereby in Step C of Panel B the chaperonin 514 has no or low binding with the protein. The lack of binding or reduced binding of the chaperonin 514 to the protein shows the stabilizer C stabilizes the first conformation 510 and inhibits transformation to the second conformation 512. The data from Panel A and Panel B of FIG. 5 can be plotted as signal versus time, where in the absence of the stabilizer C (Panel A) the chaperonin 514 binds the protein to generate a higher signal and in the presence of the stabilizer C (Panel B) the chaperonin 514 does not bind or has significantly reduced binding to the protein to generate a lower signal.

In one embodiment, the chaperonin protein can include the GroEL chaperonin protein. The chaperonin protein is able to bind transiently appearing partially folded proteins that are in dynamic equilibrium with folded states. In the presence of test protein stabilizers screens, an observed binding of the transient formed partially folded protein to the chaperonin (e.g., either bound to the BLI tip or free in solution with protein bound to the BLI tip) indicates that the test ligand does not stabilize the protein. If the candidate protein stabilizer does bind and stabilize the target protein, there is a shift in the equilibrium back toward the folded protein state, and then the assay shows that the target protein (e.g., protein of interest) no longer binds to the chaperonin. FIG. 5 shows the signal changes from chaperonin binding to transitioned protein on the tip.

Figure 6:
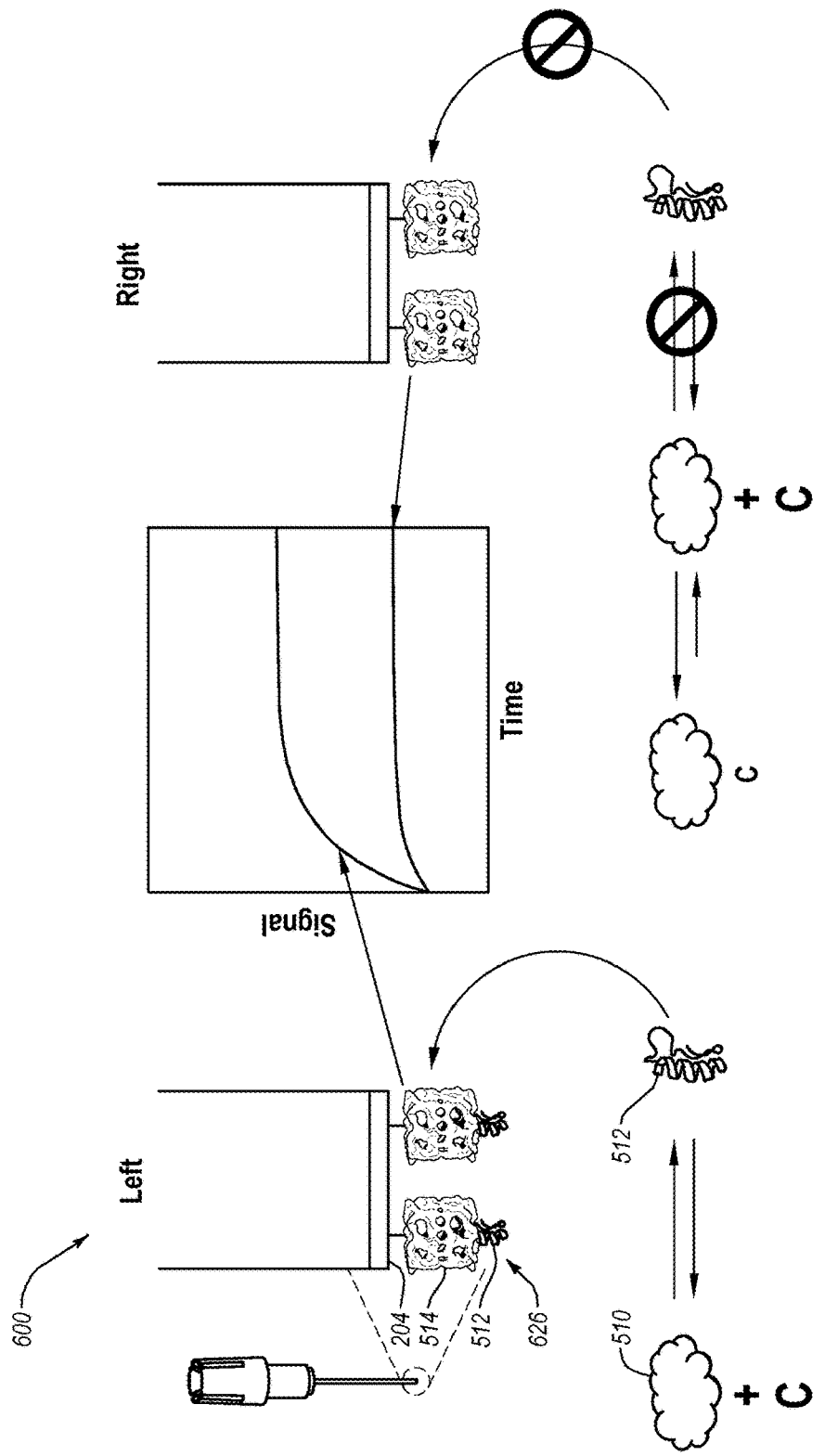
FIG. 6 illustrates an embodiment of a system and method for screening a substance for inhibiting a target protein from changing conformation and associating with a chaperonin linked to a substrate.

FIG. 6 shows that an assay 600 to determine whether or not a stabilizer substance C can inhibit conformational translation of a protein from a first conformation 510 to a second conformation 512 can be performed with a chaperonin 514 of the protein bound to a substrate surface 204. As such, FIG. 6 can be considered to be a reverse assay configuration from FIG. 5. Here, the chaperonin 514 for the transitioned conformation 512 of the protein is bound to the BLI tip substrate surface 204, where the chaperonin 514 is GroEL. However, any protein and chaperonin combination can be used. The left panel of FIG. 6 shows a protein in a first conformation 510 that undergoes a conformational translation to a second conformation 512, and the second conformation 512 allows the protein to bond with the GroEL chaperonin 514 on the BLI tip surface 204. The second conformation 512 may be a miss-folded, or mutant, or membrane inserted form (e.g., toxic transitioned). The chaperonin 514 and transitioned protein 512 form complex 626. The right panel of FIG. 6 shows the protein in the first confirmation 510 being introduced to a stabilizer C (e.g., corrector) that stabilizes the protein in the first conformation 510 so as to inhibit the protein from conformational transition to the second conformation 512. As such, the protein does not bind or has substantially reduced binding with the GroEL chaperonin 512 bound to the BLI tip surface 204. The graph of FIG. 6 shows that binding of the protein in the second conformation 512 to the GroEL chaperonin 514 produces a higher signal versus time, while the protein in the first confirmation 510 stabilized with the stabilizer C produces a lower signal versus time that indicates no bonding to the chaperonin 514. The lower signal or no signal shows the stabilizer C stabilizes the protein and inhibits conformation translation.

The chaperonin can bind to the partially folded state, at binding affinities that approach or are comparable to tight antibody and antigen interactions with the protein of interest. The chaperonin-protein binding is strong and kinetically partitions (e.g., pulls) the protein out of solution when the chaperonin is attached to the substrate. On the other hand, when the protein is bound to the substrate, the formation of a chaperonin-protein complex pulls the chaperonin out of solution. In bulk solution, this change in amount of protein, either chaperonin or protein of interest, in solution can be used for determining whether or not a substance is protein stabilizer, and the strength of the protein stabilizer.

In one embodiment, a chaperonin protein immobilized or coupled to a substrate, can be used to detect the partial unfolding transition of the target protein with the use of antibodies for the target protein. Potential stabilizers can be used to inhibit the formation of the target protein/chaperonin complex. In this embodiment, antibodies specific for the target protein will bind to the target protein that becomes bound to the immobilized chaperonin to form a chaperonin/target protein complex on the substrate, and allow one trained in the art to detect whether or not binding of a particular protein stabilizer to the target protein has occurred. The decrease in antibody binding signal can identify potential protein stabilizers that could be further tested to confirm the substance is a protein stabilizer by secondary screens as described herein (FIG. 7).

In one embodiment, the present invention can include a process for the detection of a bound protein to a chaperonin of the protein after it has partitioned. This is particularly useful in situations where a dissociation of an oligomeric protein to a monomer that can now bind to the chaperonin, which now can be detected even when the dissociation is slow. For example, one can incubate the chaperonin tip with the dissociating dimer, and then at various times, dip the tip into an Ab solution which enhances the corresponding signal.

Figure 7:
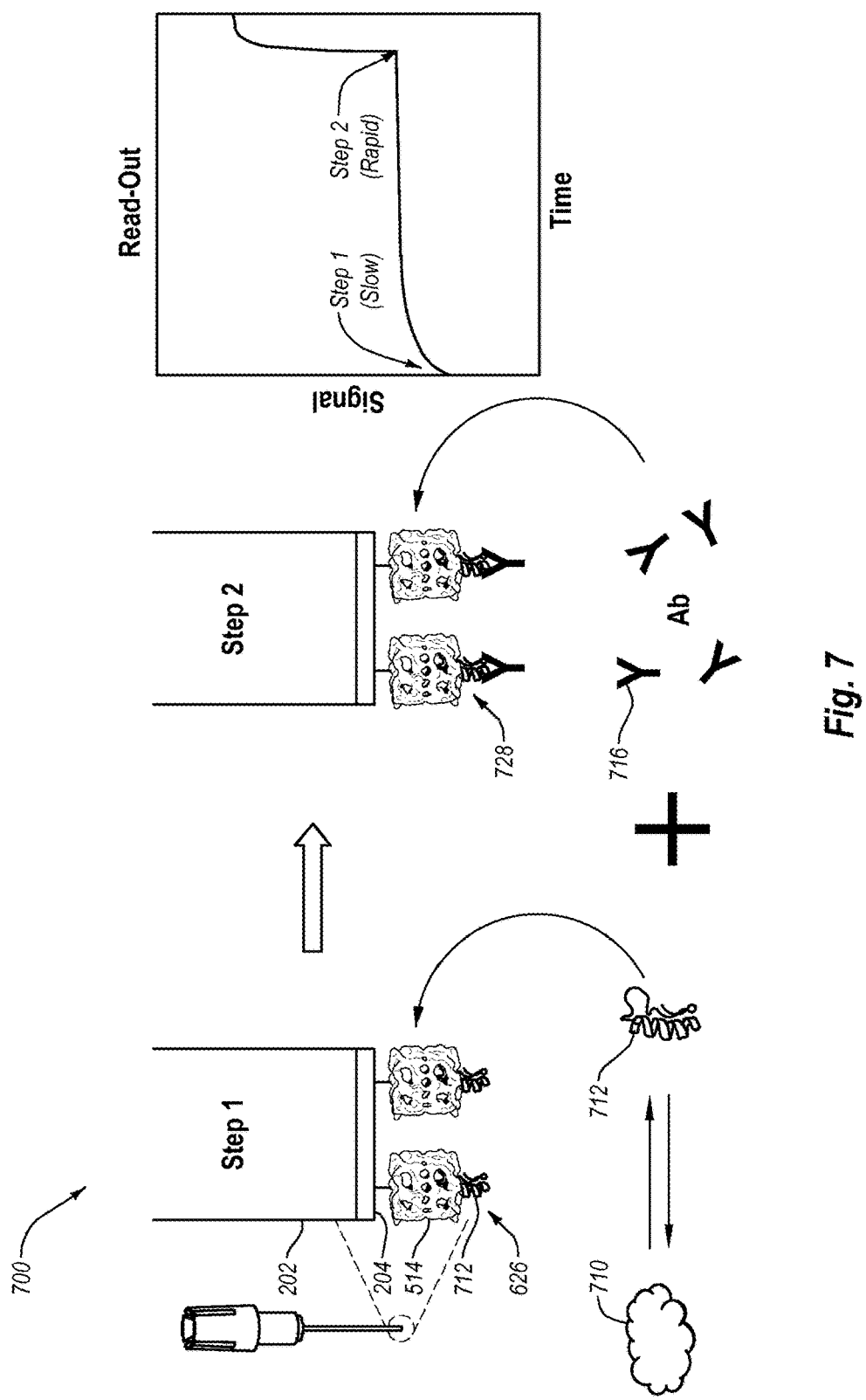
FIG. 7 illustrates an embodiment of a system and method for using antibodies to enhance the signal associated with binding a target protein to a chaperonin bound to a substrate and determining if test stabilizers are effective for preventing a changing conformation and can result in the association with a chaperonin linked to a substrate.

FIG. 7 shows a process 700 of determining a protein conformation transition using an antibody for the transitioned protein 712. As shown in Step 1, a chaperonin 514 bound to a BLI tip surface 204 can be used to detect transitioned protein 712 binding followed in Step 2 with introduction of antibody 716 (i.e., Ab) with enhanced signal as per the Readout graph. FIG. 7 shows substantially the same Step 1 as in FIG. 6, and where detection of slow protein transition through binding onto the chaperonin 514 on the BLI tip surface 204, where the folded protein 710 does not bind with the chaperonin 514. Step 2 of FIG. 7 shows that the BLI tip surface 208 having the chaperonin 514 bound thereto is dipped into a solution with antibodies 718 for the transitioned protein 712, and where the antibody 716 binding to the target transitioned protein 712 enhances detection of transitioned protein 712 on the chaperonin 514. This enables the ability to detect whether or not the chaperonin protein 514 becomes bound to the antibody 716 to form a complex 728. The graph of FIG. 7, which is a BLI readout, shows that step 1 produces a slow, small signal and step 2 produces a rapid, larger signal. This also shows a detection scheme for both rapid and slowly binding proteins where the binding to the chaperonin 514 is limited by the overall slower transition. While not shown, a stabilizer can be introduced into the chaperonin and/or target protein to inhibit their association. The stabilizer then can inhibit the antibody from associating with the previously transitioned but now stabilized protein (510+C) as observed in FIG. 6 which in turn inhibits the increase of signal shown in the graph.

In one embodiment, a capture protein can be bound to the substrate and then introduced to a potential stabilizer. The potential stabilizer can bind with the capture protein. The substrate having the capture protein and potential stabilizer can then be introduced to a target protein. If the capture protein binds with the target protein, the potential stabilizer does not inhibit transformation (e.g., does not stabilize target protein) of the target protein from a first conformation to a second conformation. If the capture protein does not bind with the target protein, the potential stabilizer is a stabilizer that inhibits transformation (e.g., stabilizes the target protein) of the target protein from the first conformation to the second conformation.

Figure 8:
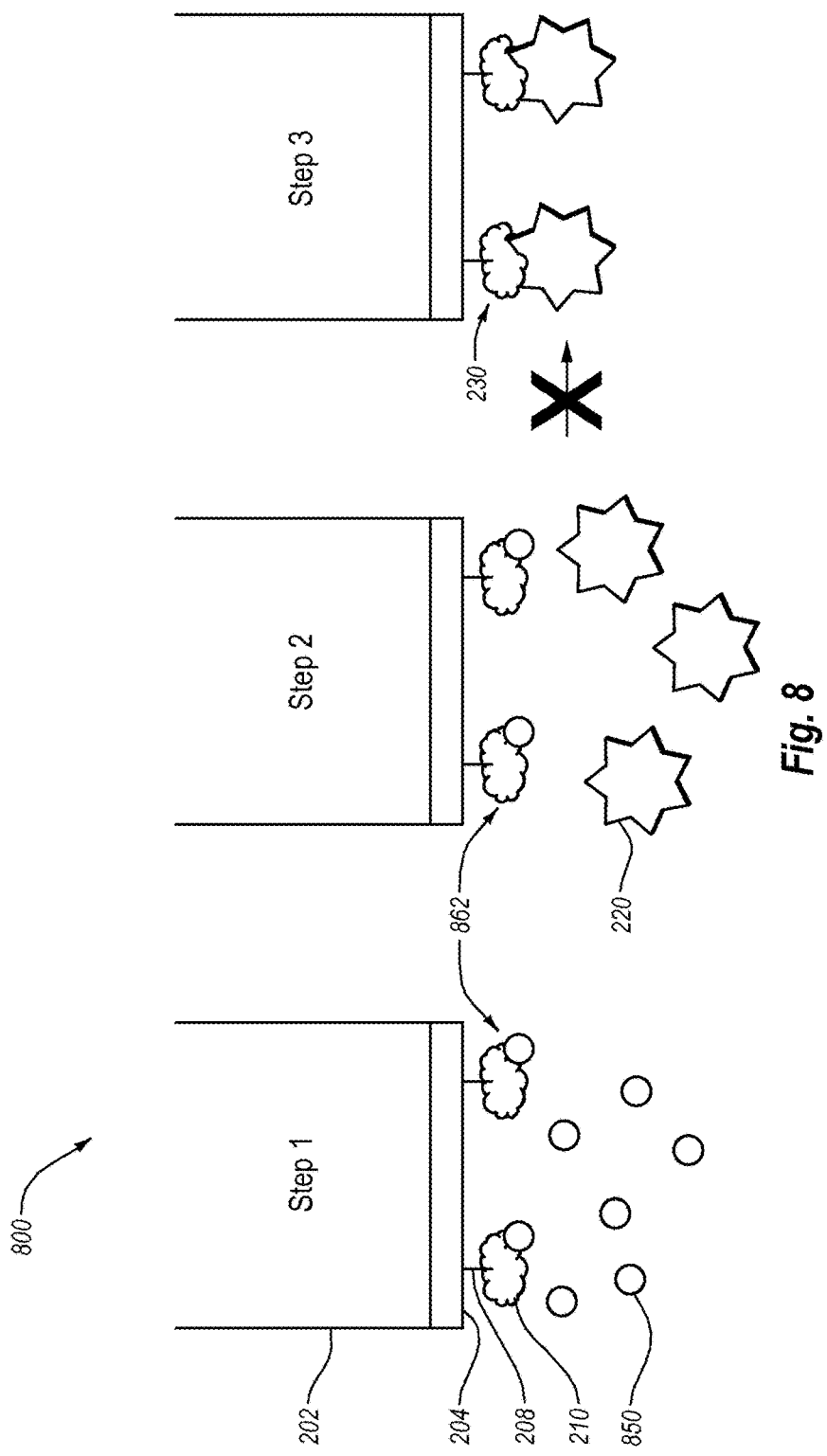
FIG. 8 illustrates an embodiment of a system and method for screening a substance for inhibiting a target protein linked to a substrate from associating with another protein (e.g., chaperonin or Hsp proteins or bacterial toxin proteins).

FIG. 8 shows a process 800 of identifying a substance that can inhibit toxic complex formation. As shown, a capture protein 210 (e.g., LFN) linked to a surface 204 of a substrate 202 via a linker 208 to assay for potential inhibitors 850 of a toxin complex formation. Step 1 of FIG. 8 includes a potential inhibitor 850 being introduced to the capture protein 210 and binding thereto to form a complex 862. Step 2 of FIG. 8 includes introducing an anthrax prepore 212 (e.g., target protein) to the complex 862. If the potential inhibitor 850 inhibits formation of a complex 862 between the capture protein 210 and the target protein 212, then no complex is observed in Step 3. That is, the prepore 212 does not change conformation to the pore 214 in the anthrax example (FIG. 2). This shows an example of a screen for inhibitors (e.g., stabilizers) that inhibit toxin complex formation. Preventing initial toxin complex (e.g., LFN/prepore) formation can provide a prophylactic agent.

In one embodiment, a linker antibody (e.g., anti-mouse antibody) can be attached to the substrate, which is then introduced to a capture antibody (e.g., CFTR antibody), and which is then introduced to a target protein (e.g., cystic fibrosis transmembrane conductance regulator, CFTR). In some instances the capture antibody can be linked directly to the substrate or through a suitable linker. However, the linker antibody can position the capture antibody a suitable distance from the substrate by antibody extension. If no stabilizer is present, a chaperonin (e.g., GroEL) can bind with the target protein to provide a large signal. If a stabilizer is present, the chaperonin does not bind with the target protein and provides a low signal. A decreased binding signal shows a stabilizer stabilizes the target protein from transforming to a conformation that binds with the chaperonin.

Figure 9:
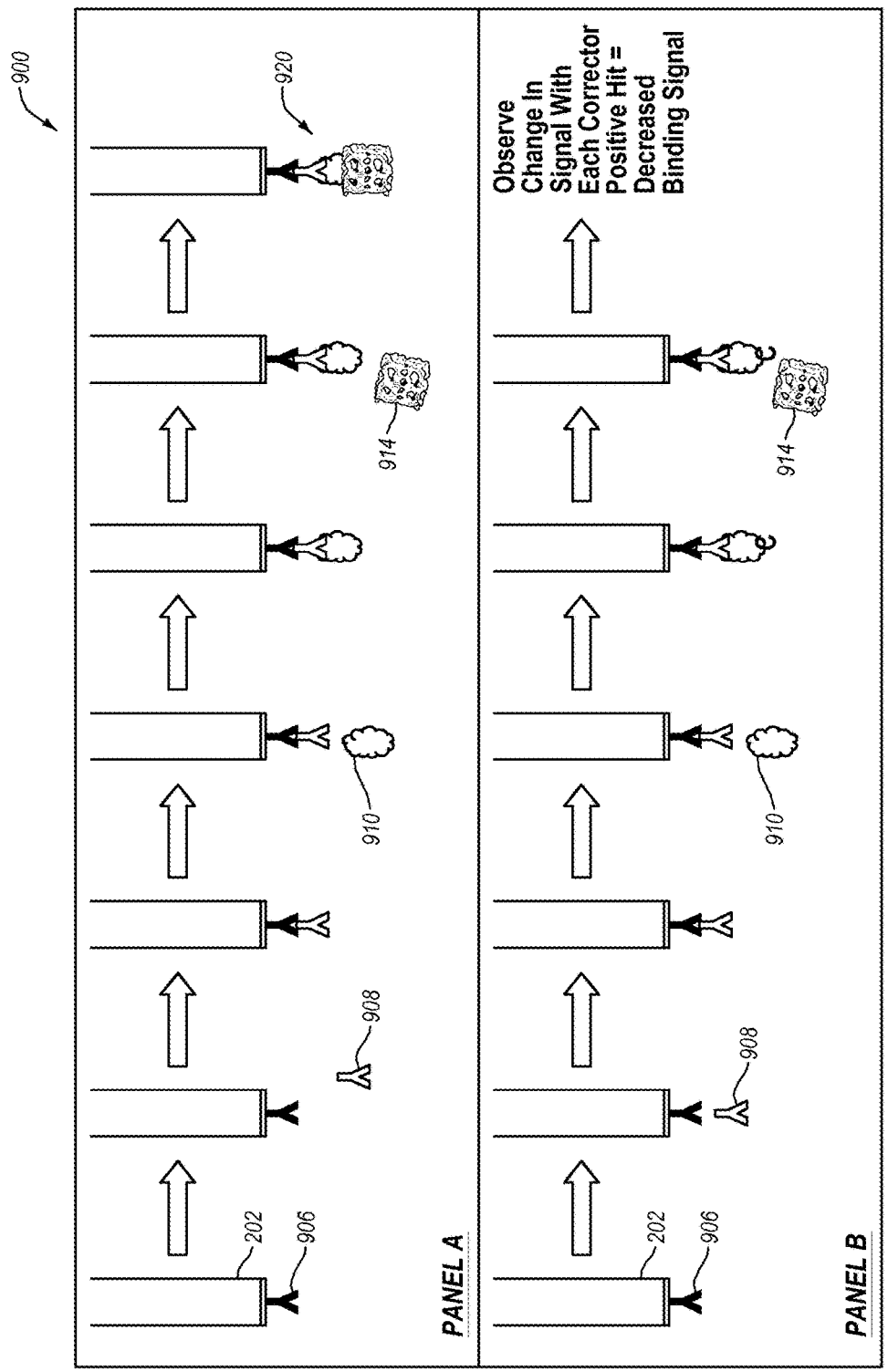
FIG. 9 illustrates an embodiment of a system and method for screening a substance from inhibiting a protein linked to a substrate from interacting with a chaperonin.

FIG. 9 shows a process 900 for determining whether a stabilizer C can inhibit a chaperonin 914 from binding with CFTR 910. As shown, a substrate 202 has an anti-mouse antibody 906 bound thereto. Then, a CFTR antibody 908 is associated with the anti-mouse antibody 906. CFTR 910 is then introduce to and bound with the CFTR antibody 908 before a chaperonin 914 (e.g., GroEL) is introduced to the CFTR/CFTR antibody complex. Panel A of FIG. 9 shows the system when no stabilizer C is present and Panel B shows the system when a stabilizer C is introduced to the CFTR/CFTR antibody complex before being introduced to the chaperonin 914. When there is no stabilizer C, the chaperonin 514 binds with the CFTR/CFTR antibody complex to form complex 920 and to produce a large signal. When the stabilizer C is present, there is a decreased binding signal to indicate that the chaperonin cannot bind with the CFTR/CFTR antibody complex.

FIG. 7 also shows a GroEL chaperonin 514 that can be bound directly to the substrate. Then, the CFTR 710 is interacted and associated with the chaperonin 514, which produces a lower signal. When the CFTR antibodies 716 are intruded to the CFTR/chaperonin complex 726, the biding signal is significantly increased as shown in the graph. As such, binding of CFTR antibody 716 to the GroEL-CFTR complex 726 can increase the interference leading to a larger signal with larger amplitude.

Additionally, the CFTR nucleotide binding domain (e.g., CFTR-NBD1) may be bound directly to the substrate, which is then introduced to a GroEL buffer. When the CFTR-NBD1 is introduced to GTP prior to being introduced to GroEL, there is no signal or a low single. When the CFTR-NBD1 is not introduced to GTP prior to being introduced to GroEL, there is a much higher single. Other substances besides GTP can also be screen to identify inhibitors of forming the CFTR-NBD1/GroEL complex. Also, it should be noted that GTP does not bind to the GroEL chaperonin.

The kinetics of the CFTR-GroEL interaction was studied with different amounts of GroEL. The data showed that the higher amount of GroEL (e.g., 4 µM) had the highest signal, followed by 2 µM, 1 µM, 0.5 µM, and 0.25 µM, and where 0 µM produced almost no signal. As such, the more GroEL, the higher signal amplitudes and kinetics of the interaction and complex formation.

In one embodiment, the present invention can find destabilizers that destabilize target proteins and allow for transition from a first conformation that does not bind with a capture protein or chaperonin to a second conformation that does bind with the capture protein or chaperonin. The capture protein or chaperonin can be bound to the substrate, and the target protein can be in solution with or without a potential destabilizer. When with a destabilizer, the target protein transforms from the first conformation to a second partially folded or destabilized conformation that can now bind to the capture protein or, in this instance, the chaperonin. When not with a destabilizer, the target protein does not transform to the second conformation and does not bind with the capture protein or chaperonin.

Generally, a protein destabilizer as described herein is the direct opposite of a protein stabilizer in that the protein destabilizer promotes a protein conformation transformation that results in the exposure of hydrophobic patches wherein chaperonin binding can now occur. Instead of assaying for substances that inhibit the protein conformation transformation, the assay looks for substances that actually promote the protein conformation transformation to a partially unfolded or hydrophobic protein. For example, this may be observable with an increase kinetic of chaperonin binding with the protein of interest in response to a protein destabilizer. The protein destabilizer may also be referred to as a protein unfolding promoter. Also, the destabilizers can be used for analyzing de-aggregation of aggregated protein monomers. This approach will be useful for screening for destabilizers of HSP 90 cofactors, which can eventually be used for anticancer drugs for example (FIG. 10).

Figure 10:
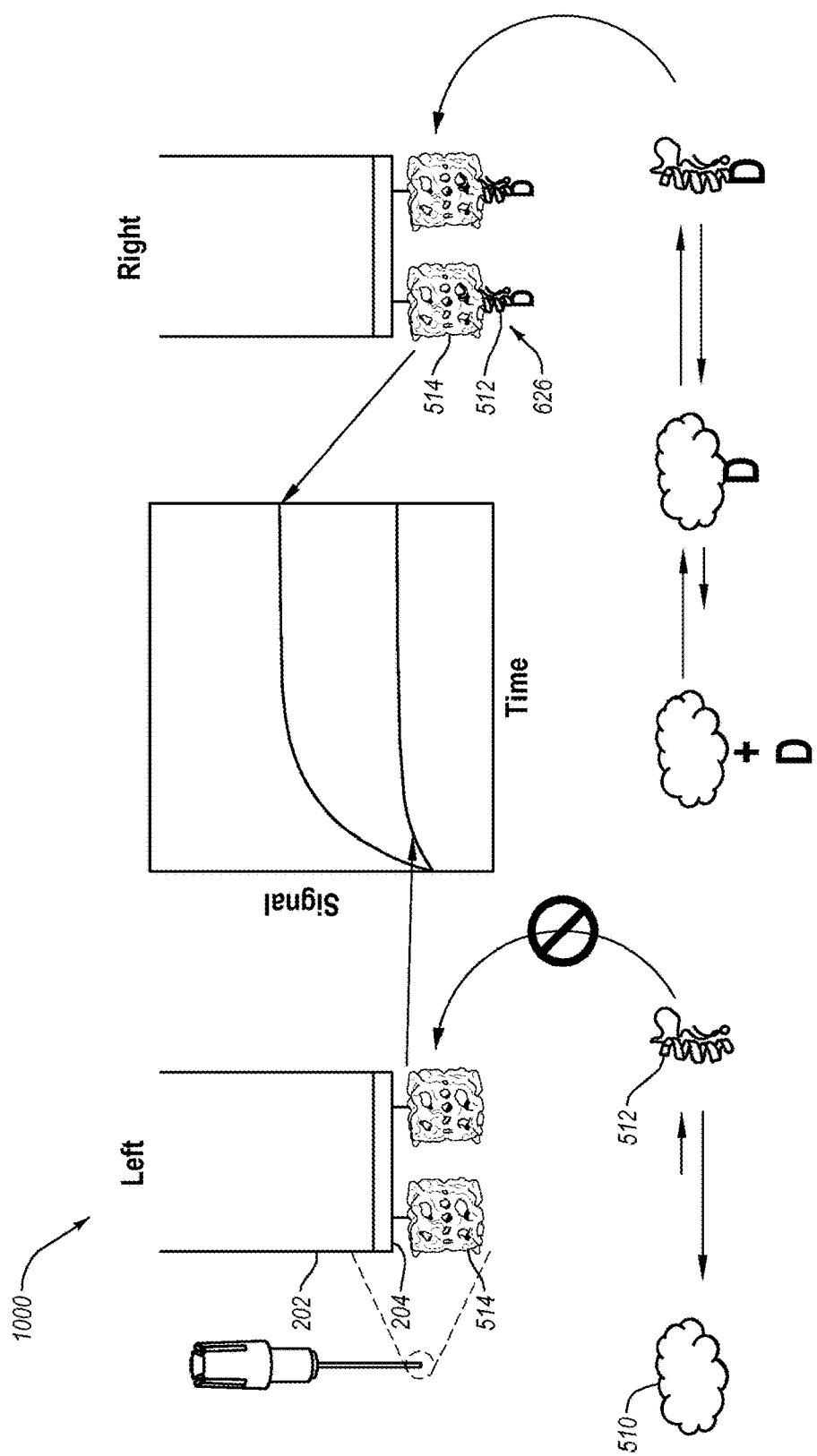
FIG. 10 illustrates an embodiment of a system and method for screening a potential destabilizer for destabilizing a protein or protein complex.

FIG. 10 illustrates a process 1000 of using a reverse reaction where one would be looking for an enhanced binding of a transitioned protein 512 due its interaction with a small molecule destabilizer D. Here, the folded protein 510 (e.g., HSP 90 cofactor) does not interact with a chaperonin 514 bound to a substrate 202 as shown on the left panel. The folded protein 510 does not readily change to the transitioned protein 512. The right panel shows a destabilizer D introduced to the folded protein 510 so as to promote conformation transformation to the transformed conformation 512, where the transformed conformation 512 interacts with the chaperonin 514 on the substrate to form complex 626. The graph of FIG. 10 shows the left panel as a low signal showing no or lower binding, and the right panel has a high signal showing higher binding. The destabilizer D can thereby promote binding to chaperonin.

Figure 11:
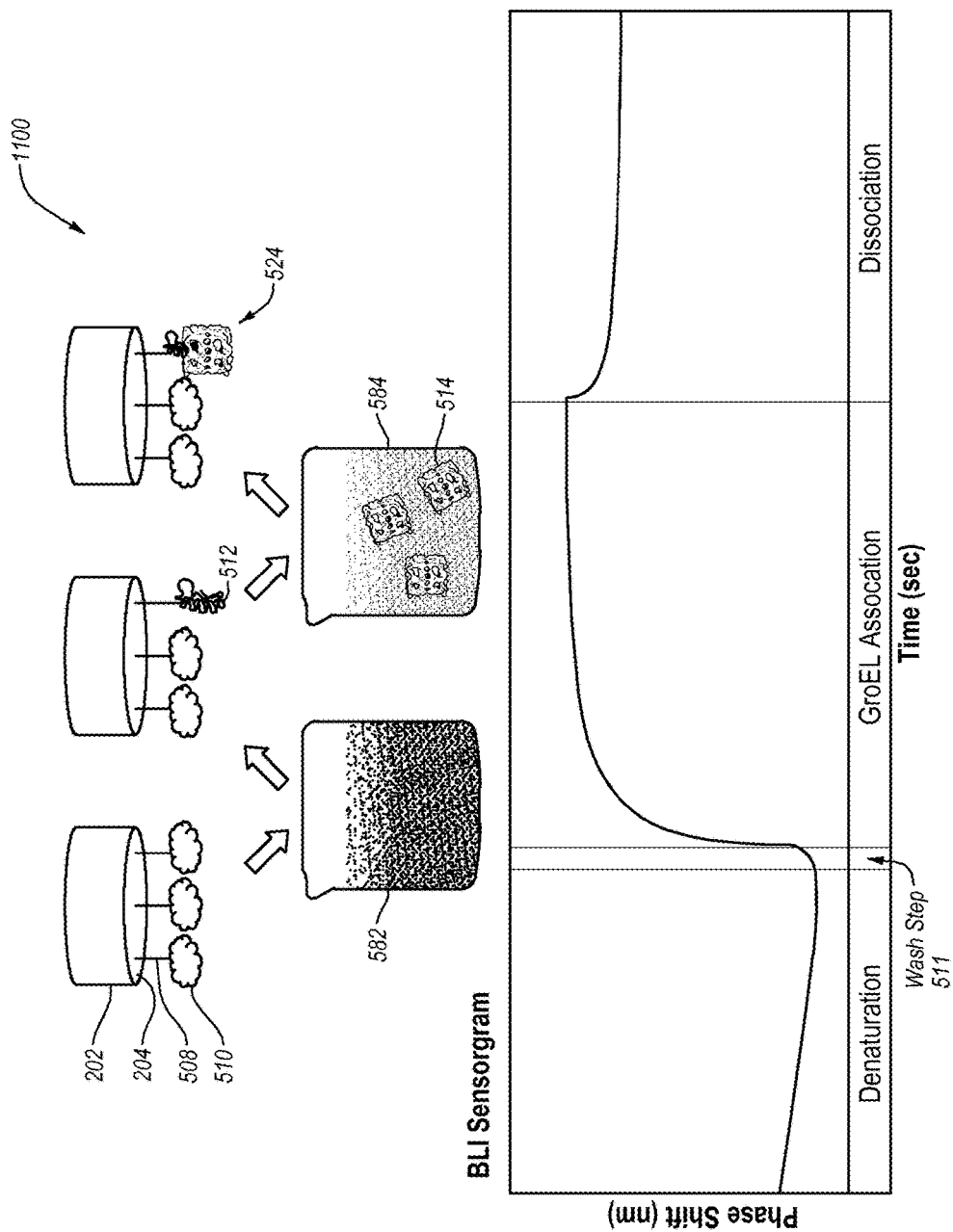
FIG. 11 illustrates an embodiment of a system and method for using a denaturant to enhance reaction kinetics of the processes of the present invention.
Figure 12A:
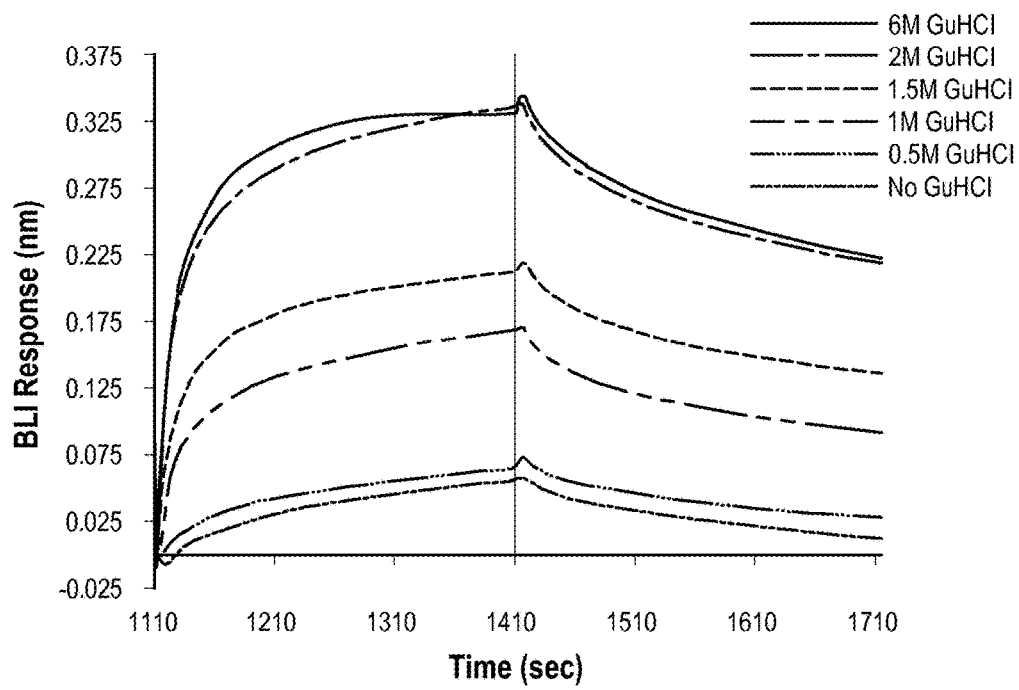
FIG. 12A includes a graph that illustrates a denaturant concentration change study for the process of FIG. 11.
Figure 12B:
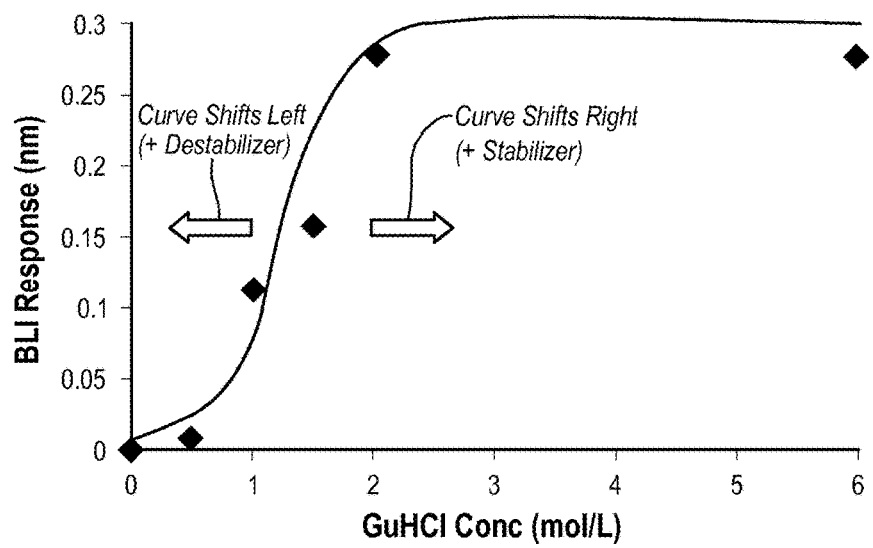
FIG. 12B includes a graph that illustrates a kinetic denaturation curve for the process of FIG. 11.

FIG. 11 illustrates a process 1100 can be used to identify protein stabilizers that prevent or slow protein unfolding following a brief exposure of an immobilized protein substrate in a first conformation 510 (e.g., folded protein) on the surface 204 of a substrate 202 (e.g., SPR chip or BLI biosensor surface) to increasing concentrations of denaturants including acidic or basic pH changes, urea, GnHCl or GnSCN, as well as any other protein denaturant. In this process, the folded protein 510 is first immobilized via any number of common coupling chemistries involving covalent or noncovalent linkages described herein, including S—S (disulfide bonds) linkages such as described in connection to FIG. 1. Also, the system can include the components described in connection to FIGS. 2 and 5 as well as a denaturant solution 582 and a chaperonin solution 584 having chaperonins After immobilization, the folded protein 510 is briefly dipped or exposed to a pulse of denaturant or denaturing conditions (e.g., denaturant solution 582) for a specified period of time whereby a population of the attached folded protein 510 will begin to unfold and denature into a second conformation 512 (e.g., transitioned protein). After this timed exposure, the substrate 202 having the proteins 510, 512 is exposed to a brief neutral buffer wash solution at pH 7 for 5 to 10 sec at step 511, followed by an introduction to a chaperonin solution 584 having a chaperonin 514 (e.g., GroEL). Washing before introducing to the chaperonin 514 keeps the chaperonin from denaturing or otherwise being compromised and not being functional. Any protein that has unfolded or is partially folded into a transitioned protein 512 can bind the GroEL chaperonin 514 to form a complex 524 and can produce a large signal deflection in amplitude. The amplitude of the GroEL binding is plotted against increasing denaturant concentrations to generate a kinetic denaturation curve as shown in FIG. 12B. Also, the concentration of the denaturant (e.g., GuHCL) in the denaturant solution 582 can be varied, so that the response can be graphed as shown in FIG. 12A.

Figure 13:
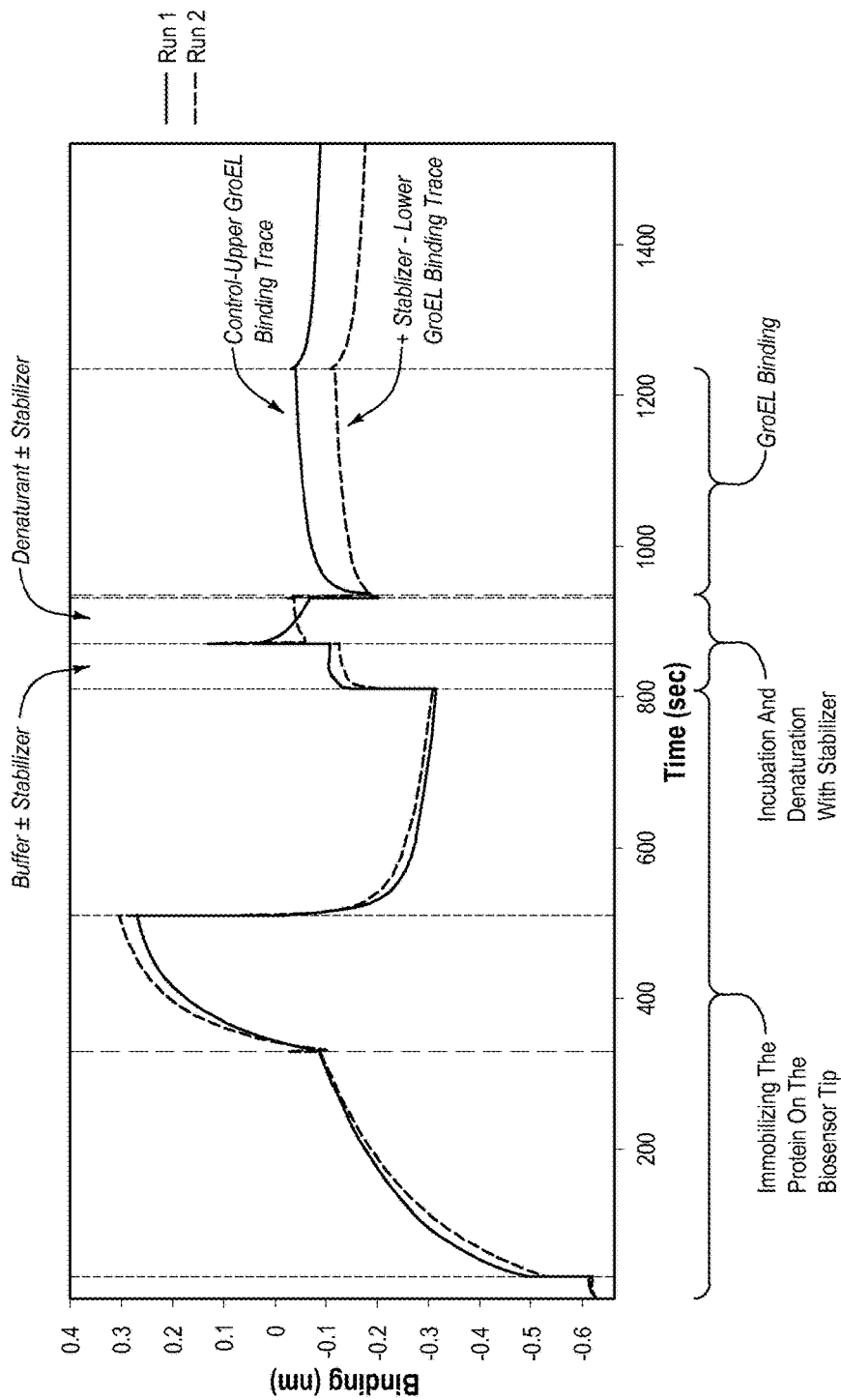
FIG. 13 includes a graph that illustrates binding over time when using the system of FIG. 11 to screen potential protein stabilizers.

Once this kinetic denaturation curve is generated, in a test sample, one can then introduce a potential stabilizing substance, as described herein, to the immobilized protein in neutral buffer before exposing the protein to the denaturant concentration. The potential stabilizing substance can also be included within the denaturant solution 582 to slow the denaturation rate if the potential stabilizing substance stabilizes the immobilized folded protein 510. Alternatively, the stabilizing substance can be in wash buffer to stabilized folded proteins 510 that have not unfolded to the transitioned protein 512, and the stabilizing substance may also be included in the chaperonin solution 584. Following the same procedure of a brief wash to removed denaturant (and excess ligand), the immobilized protein is exposed to the GroEL chaperonin solution. If the folded protein 510 is stabilized by the potential stabilizer being screened, the amplitude observed from GroEL chaperonin 514 binding to form the complex 524 will be decreased denoting the situation where the folded protein in question is stabilized by the potential stabilizer as shown in FIG. 13. In the presence of a stabilizing ligand, the kinetic denaturant curve can shift rightward or downward indicating that the potential stabilizer in question stabilized the immobilized folded protein 510.

Alternatively, a test ligand may also actually destabilize the immobilized folded protein 510 substrate resulting in an increase in the GroEL binding amplitude and resulting in a leftward or upward shift in the kinetic denaturation curve.

An advantage of process 1100 may be the usefulness and accuracy that may omit any secondary or conformation screening due to stabilizer or destabilize interference with chaperonin binding. That is, the use of the denaturant may provide data that can stand alone without secondary conformation. As such, the process 1100 can be performed without a secondary control screen with another protein (e.g., DHFR) to test for ligand binding interferences with GroEL binding. In part, this is because the denaturant pulse and read procedure of process 1100 can examines GroEL binding with the target folded protein 510 in the absence of a stabilizing ligand or solution conditions. Process 1100 can be useful for searching for any protein stabilizing substance for protein toxins as well as stable proteins that do not normally populate substantial unfolded protein species. Examples of test proteins include proteins that exist as monomers (e.g., single polypeptides), multimeric proteins (e.g., multiple subunits), heterologous assembled protein complexes as well as the entire list of toxin proteins described herein or generally known or discovered. This particular procedure 1100 can work for all proteins that are stably folded but unfold once exposed to common chemical denaturations.

Figure 14:
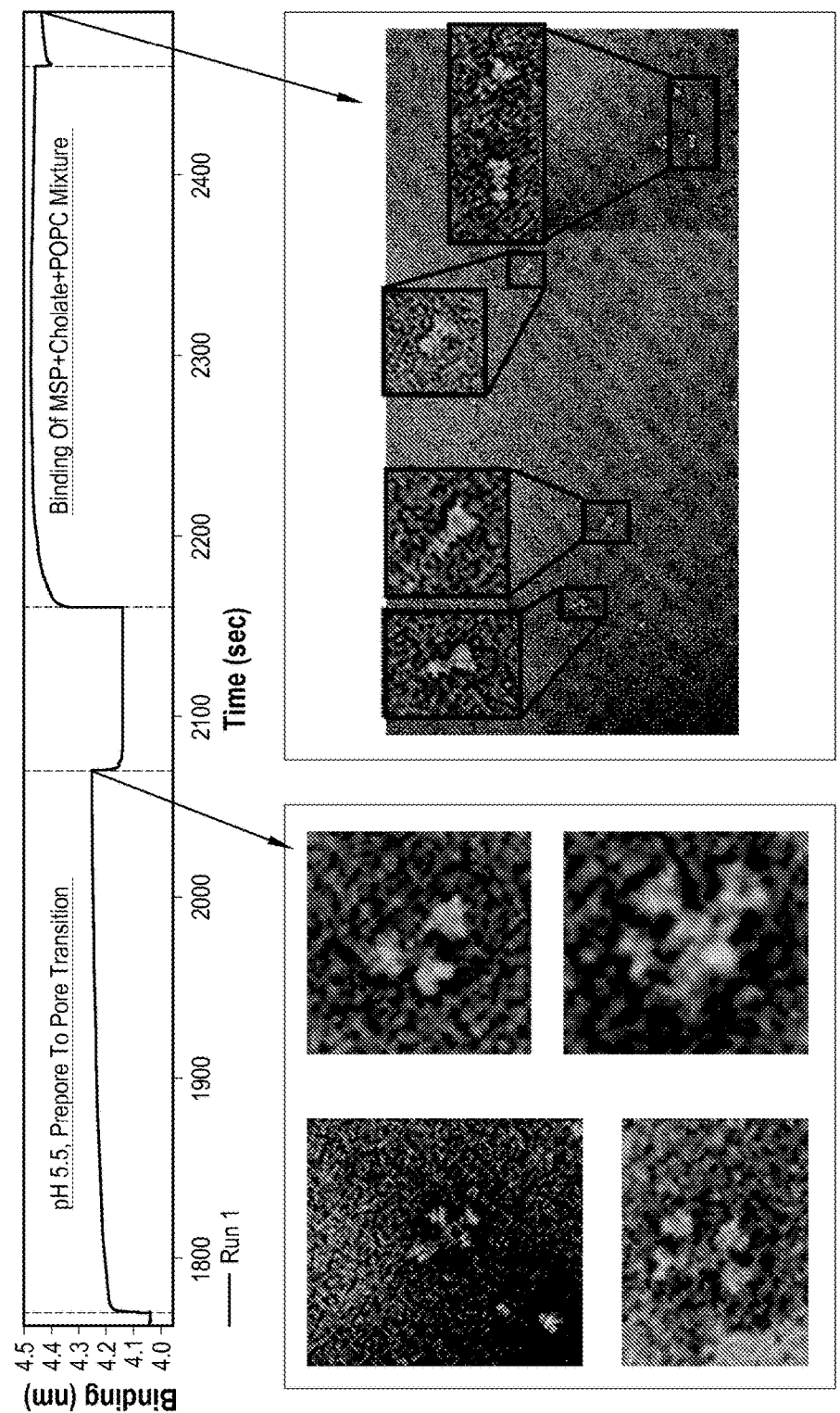
FIG. 14 includes a graph and images that illustrate an amplification of a signal from a protein transition from soluble to membrane inserted conformation followed by micelle binding.

In one embodiment, the present invention can also include a process for amplification of a signal obtainable for soluble protein conformation (e.g., first conformation) to a membrane-inserted protein conformation (e.g., second conformation) transition following micelle binding. Generally, the micelle binding can be used substantially similarly to the use of the chaperonin described herein. After the immobilized toxin or protein undergoes a transition from a folded form to its membrane-inserted (e.g., membrane-insertable) form, the transitioned protein can be exposed to a defined micelle having a matrix scaffold protein, cholate, and phospholipids as well as other common micelle substances. The micelle can bind to the exposed membrane-insertable region, and generate an observable label free signal (e.g., with SPR or BLI). If the transition does not occur, this confirmatory deflection of the transition itself or the formation of newly exposed membrane-insertable regions that can bind to micelles may not be observed as shown in FIG. 14. Particularly, FIG. 14 shows data from monitoring insertion of an anthrax protective antigen (PA) into a lipid micelle on immobilized solid BLI tip surface after prepore to pore transition. The graph of FIG. 14 on the left side shows data for pH 5.5 with prepore to pore transition, and the corresponding TEM images of the released PA pore from the BLI probe indicate the PA pore aggregates are present. The now free PA pores aggregate because the exposure unprotected membrane insertion portion of the toxin interact with each other creating mini aggregates shown on the left hand TEM image. The right side of FIG. 14 shows the binding of MSP+cholate+POPC mixture, and the corresponding TEM images indicate insertion of PA into the lipid micelle, resulting in unaggregated individual and distinguishable anthrax toxin pores. Furthermore, if the protein is large enough in size and the immobilization is reversible, the protein complex can be released from the biosensor, wicked onto an EM grid and examined using electron microscopy as shown in the images of FIGS. 14-15.

Figure 15:
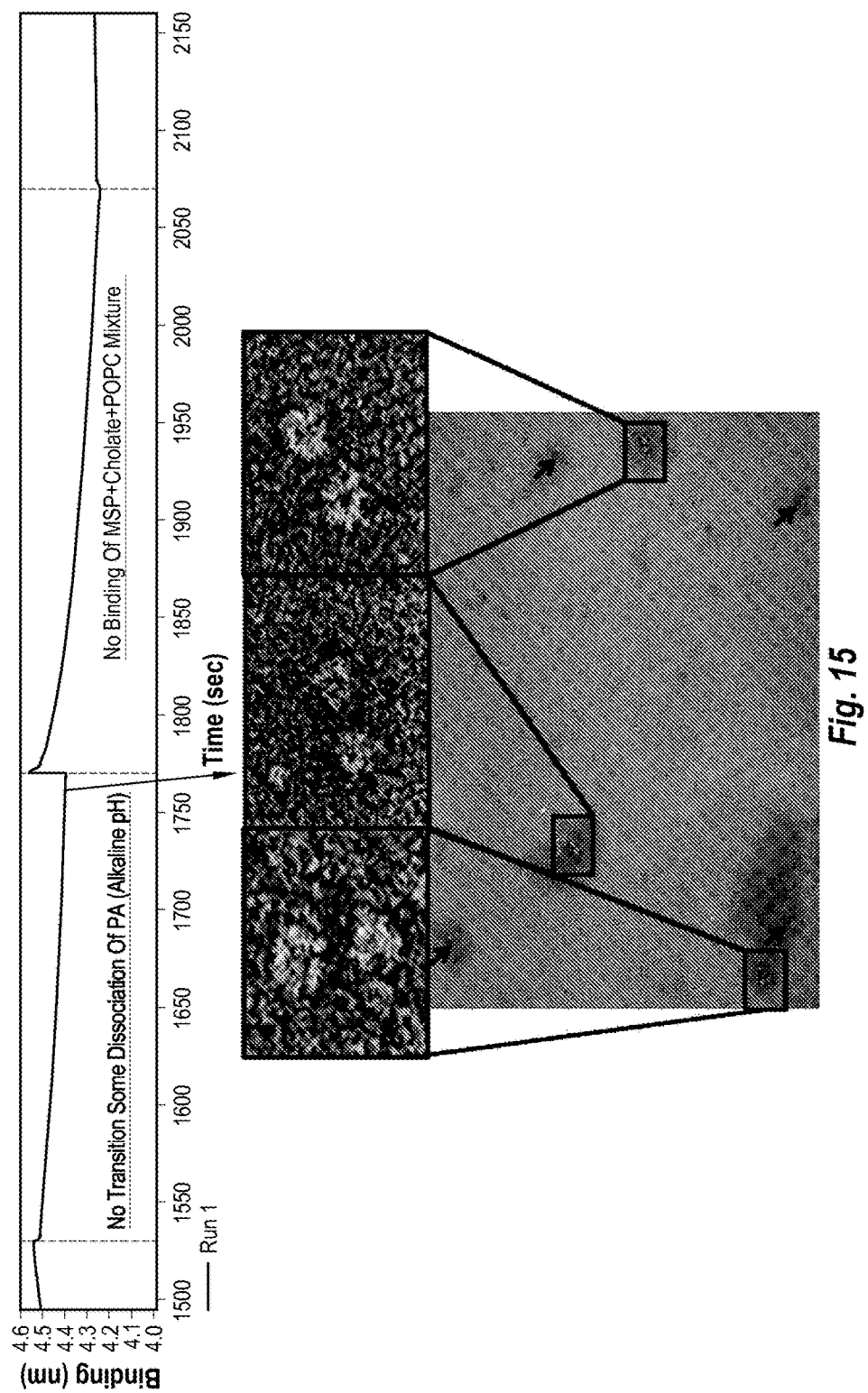
FIG. 15 includes a graph and images that illustrate a control with no micelle binding according to the process of FIG. 14.

FIG. 15 shows results of a control experiment that indicate that no insertion of lipid micelles/nanodisc occurs without prepore to pore conformation transition from a change in pH 7 to 8. FIG. 16 can be directly compared to FIG. 14. By this procedure, the transition of the anthrax toxin from its soluble form to its membrane inserted form or lack of the transition unfolding and refolded can be visually verified. This procedure can also be used with a nanodisc or micelle linked to a substrate as described herein.

Accordingly, the processes described herein can be used with micelles in order to enhance the signal output when the protein transitions conformation. Adding a micelle can coat the now exposed membrane insertable regions. The micelle can be used with or without the chaperonin. In one instance, the micelles are used in place of the chaperonins as described herein. The micelle can also be used in instances the chaperonin cannot bind with the transitioned protein, possibly due to the protein and chaperonin having the same charge and repelling (e.g., negative/negative).

In one embodiment, the invention can include compositions, systems and methods configured for performing affinity-based analysis of protein conformation transformation as well as inhibition thereof. This can include the immobilization of a protein capable of undergoing a conformation transformation. For example, a system can include a substrate, such as a probe (e.g., BLI) or a well bottom (e.g., SPR), which includes a protein (e.g., bacterial toxin, such as LFN) thereon. The immobilized protein can be considered to be a capture protein because it binds or otherwise interacts with other proteins such as the prepore and pore so as to capture. The substrate having the capture protein can then be used to detect the unfolding and refolding transitions of other proteins that interact with the capture protein, such as toxins and viral proteins, which occur during viral/bacterial infections.

In one embodiment, the present invention can be used for identifying protein stabilizers that can stabilize a target protein for purposes of drug discovery, such as discovering potential drugs for use in: inhibition (e.g., anti-toxin) of conformational transition studies, prophylactic antibacterial studies, prophylactic antiviral studies, small molecule chemical screens, natural product chemical screens (e.g., nutraceuticals), small molecule metabolite screens, toxin conformation transformation studies, soluble to membrane insertion studies, and other protein unfolding and refolding studies, as well as others. The protein stabilizer can also be a ligand for the target protein.

In one embodiment, the systems and methods can be used to monitor water soluble to membrane soluble conformational transition for one or more target proteins in real time. In one aspect, the monitoring of target protein conformation transformation can be performed without aggregation of the target proteins before, during or after conformation transformation. As such, the target protein being studied for conformation transformation can be immobilized on a substrate as described. The immobilization on the substrate can be by any method of protein immobilization known or later developed, such as including direct amine coupling, antibody capture, and biotin/streptavidin affinity among others. For example, this can include the affinity immobilization of a target protein, such as the prepore (e.g., water soluble form) conformation of the anthrax toxin pore using an N terminal lethal factor construct.

In one embodiment, the target protein conformation transformation can be monitored in real time in any pH condition. Similarly, the screening of potential protein stabilizers that inhibit or prevent protein conformation transformations can also be screened in any pH condition. As such, a drug library or potential drug library can be screened to identify small molecules that function as protein conformation transformation inhibitors that inhibit the transition at a certain pH or across a broad pH range.

It can be desirable to identify and test a known protein stabilizer (e.g., control) or potential protein stabilizer (e.g., potential drug) that functions as a protein conformation transformation inhibitor at any pH. The most effective protein confirmation transformation inhibitor can be a compound that can bind tightly at both pH 7 and pH 5.5 environments, and inhibit the conformation transformation under both conditions.

In one embodiment, the systems and methods can only use a portion of a particular protein being studied for conformation transformation and protein stabilizers that inhibit or prevent such conformation transformations. The portion of the protein being studied can be one that is relevant in a conformation transformation. For the anthrax example, the prepore-lethal factor-soluble receptor portion complex can be used as an initial system to identify inhibitors of the pore transitions that occur as the endosome pH transitions from pH 7 to the final pH 5.5-5.0 environment. A large number of bacterial and viral proteins involved in cell penetration and transport depend on pH dependent transitions that occur during the acidification of the endosome.

In one embodiment, a control protein stabilizer (i.e. folding osmolytes) for a particular protein can be used for a positive control study. The control protein stabilizer can be a known stabilizer for a particular protein that inhibits confirmation transformation. The control protein stabilizer can be a biological molecule that naturally inhibits one or more proteins from conformation transformation. Alternatively, the control protein stabilizer can be a small molecule that is found with the screening methods described herein, wherein a confirmed protein stabilizer can then be used as a positive control to identify additional, and possibly better protein stabilizers. In the case of toxin proteins, both stabilizers and/or small molecules stabilize a non-infectious form (e.g. stabilize anthrax PA prepore form) and/or inhibit toxin complex formation (e.g. anthrax toxin pore assembling with lethal factor or edema factor prior to cell transport).

In one embodiment, the present invention can include systems and methods for high throughput screening applications described herein in order to identify stabilizing compounds (e.g., small molecule stabilizers) to inhibit protein conformational changes. Specific high throughput screening can find stabilizing compounds that stabilize a protein and inhibit either bacterial or viral toxins or surface proteins from transitioning from soluble to membrane inserted conformations. Examples of the proteins for which stabilizing compounds can be found can include anthrax proteins, clostridia toxins, MRSA secreted toxins (e.g. SA alpha toxin), viral proteins, influenza proteins, hemagluttin, or the like.

In one embodiment, the present invention can include methods of preparing the protein to be studied for conformation transformation or methods of preparing the chaperonin protein. The methods can also include techniques for binding the protein of interest or the chaperonin protein to the substrate, such as the BLI probe. The protein can also be generated in a wild-type of recombinant format.

In one embodiment, the protein conformation transformation studies with or without screening for protein stabilizers can be conducted in the presence of stabilizing osmolytes. Stabilizing osmolytes can be used as described herein. Optionally stabilizing osmolytes can be used as controls in control studies to demonstrate that the approach of identifying a stabilizer results in an observable change in signal, signifying stabilization has been achieve or protein transformations have been inhibited.

In the label-free technologies, the chaperonin is very large (802 kDa), so it generates a large signal that is easy to detect with instrumentation common in screening, as exemplified by BLI and SPR technologies, which technologies are incorporated herein by specific reference. When the signal is large, the chaperonin is bound to the protein that is immobilized on the substrate. The use of the chaperonin can allow identification of protein stabilizers at acidic physiological or neutral physiological conditions.

In another embodiment, a protein substrate may bind to the chaperonin that is bound to the substrate generating an observable signal. As a further enhancement of signal, a specific antibody to the target protein (e.g., protein of interest) can subsequently be added and a larger enhancement of signal can be observed since the antibody is also large (150 kDa). In this instance, one can use the chaperonin binding surface to bind and partition slower cycling stability proteins, which can be particularly relevant for disease proteins that show slow aggregation, to detect partitioning over longer assay periods. This particular configuration can be used as a detection method for partially folded disease proteins in biological fluids (e.g., spinal fluid, serum, cell extracts or others).

In one embodiment, the chaperonin can be used as a diagnostic tool to identify partially folded proteins in biological fluids. The partially folded proteins can bind with the chaperonin and analyzed as described herein, such as when the chaperonin is linked to a substrate and antibodies to specific target proteins (e.g. Alzheimer's protein $\alpha\beta$ peptide) are then introduced, resulting in an enhanced BLI or SPR signal.

In one embodiment, the systems and method can include adding urea (~1-2 M urea) to the composition having the protein of interest. A small amount of urea won't completely denature the protein, but it can increase the dynamic equilibrium between the folded state and the partially folded state. A urea dose can increase the kinetics and increase the speed of the processes as described herein. The amount of urea or other denaturant can be varied. This provides for increased sensitivity particularly for proteins that do not populate a transient partially folded state to a large extent. Under these slightly denaturing conditions (e.g., increased generation of a transiently folded protein population), a protein stabilizer or protein ligand interaction can be examined with a properly folded protein. This latter approach can be used to test general drug protein interactions.

To further generate and enhance the kinetic transitioning to a partially folded state, the temperature can be elevated to slightly above normal body temperatures (e.g., 40-45° C.) in addition to using sub-denaturing urea concentrations (e.g., 1 M urea). Under these conditions the chaperonin does not denature. In addition, various chaperonin species isolated from acidophiles, halophiles, thermophiles and pyscophiles can also be added to extend the test solution range to examine formation and partitioning of dynamic partially folded proteins.

In one embodiment, the methods described herein can be done at room temperature or near physiological temperatures (37° C.). In one aspect, the methods are performed without any heat such that the protein of interest is not heated or completely denatured to a point where the substrate becomes irreversibly during the measurement method.

In one embodiment, the systems and methods can be performed to monitor the stability of cystic fibrosis membrane regulator nucleotide binding domains, or a multitude of other folding disease proteins (e.g. alpha-synuclein, β-2-microglobulin, bacterial toxins, etc) such as those found in and the conformational transformation thereof. This can include identifying a protein stabilizer for the cystic fibrosis membrane regulator nucleotide binding domains or a multitude of other protein folding diseases. FIG. 9 show examples of detection of cystic fibrosis stabilization. Additionally, data shown in the provisional application at FIG. 12 therein incorporated herein shows guanosine triphosphate (GTP) stabilization of CFTR using scheme of FIG. 9. The data showed that chaperonin binding produced the highest signal. GTP binding to CFTR decreased the chaperonin binding and decreased the signal, but not as low as the buffer signal. This confirms that GTP is a protein stabilizer.

In one embodiment, the systems and methods can include detecting any pre-aggregate protein conformations of proteins that are destined to aggregate. That is, the systems and methods described herein can identify protein stabilizers that inhibit protein aggregation by inhibiting the formation of the preaggregation conformation. For example, a protein stabilizer can be screened to determine if it inhibits a protein from forming dimers, trimers, tetramers, or the like as well as general aggregation Inhibiting protein aggregation at the preaggregation step can be used for protein therapeutics and inhibit aggregation of the protein therapeutic so as to increase shelf life. This can also allow for high concentration formulations of proteins that traditionally aggregate by including a protein stabilizer that inhibits aggregation during storage.

In one embodiment, the chaperonin or protein of interest is not attached to a particle and not centrifuged. On the other hand, the chaperonin or protein of interest can be attached to a substrate of a macroscopic material, such as an instrument probe member, such as in BLI, or on an assay well substrate. As such, the chaperonin or protein of interest is bound to an instrument or plate operable with an instrument. The plate may be a biochemical chip having the chaperonin or protein of interest bound thereto. In one aspect substrate having the chaperonin bound thereto is introduced into a composition having the protein of interest. Alternatively, the substrate having the protein of interest bound thereto is introduced into a composition having the chaperonin. A potential protein stabilizer can be included in the composition that receives the substrate in order to determine whether or not it functions as a protein stabilizer.

In one embodiment, if the chaperonin detects the presence of the protein conformation transformation by binding to the target protein (e.g., protein target of interest), then a composition having the same does not include a protein stabilizer. If the chaperonin binds with a protein during its kinetic conformation transformation, then a composition having the same does not include a protein stabilizer. If the chaperonin does not bind or is inhibited from binding with a protein during conformation transformation, then a composition having the same includes a protein stabilizer.

In one embodiment, kinetics of chaperonin-protein binding or unbinding can be used to identify a protein stabilizer that inhibits such binding. The kinetics can be used to determine potential (e.g., binding strength) of the protein stabilizer to stabilize the protein.

In one embodiment, a composition for use with the systems and methods of the invention can include ATP, osmolyte, and chaperonin or chaperonin alone. This composition can be reused between screenings with the protein of interest being bound to the substrate, such as the BLI probe. Since the ATP/osmolyte, ATP alone, or osmolyte alone compositions induce protein substrate dissociation from the chaperonin, the chaperonin is reusable, and the same chaperonin composition can be used to screen a library of potential protein stabilizers. This element is important for situations where precious target protein is immobilized on the substrate surface (e.g. BLI tip) and can be reused for screening for small molecule protein stabilizers. In addition, for chaperonin immobilized on the substrate surface (e.g. BLI tip), the chaperonin tip can be regenerated for reuse, demonstrating reversibility and thus decreasing cost for the particular surface in question (e.g. SPR surface, BLI surface).

In one embodiment, the present invention can include a kit that includes a chaperonin composition and a substrate having a protein of interest bound thereto. The substrate can be a biochemical chip, well plate, or probe. The substrate can be configured to be immersed within the chaperonin composition or otherwise receive the chaperonin composition such that the chaperonin can contact the protein of interest. In one aspect, a kit can include a positive control protein stabilizer known for a target protein. In one aspect, the kit can include dihydrofolate reductase (DHFR) as a control. Data shown in the provisional application (FIG. 13 therein) shows an example of a control experiment where the protein dihydrofolate reductase is used as a control, which shows interaction between biotinylated GroEL chaperonin on a BLI substrate and dipping the BLI substrate into a DHFR solution. The data shows the DHFR reduced the signal, and that NADPH (e.g., 10 mM) or methotrexate can be used to decrease the signal. The combination of GroEL and DHFR and 10 mM NADPH can further reduce the signal. This shows a control to confirm the data and identification of the stabilizers of the processes described herein.

In one aspect, the present invention can include performing a secondary screen to determine whether or not a potential protein stabilizer identified as described herein is indeed a protein stabilizer that inhibits protein conformation transformation. As such, the secondary screen can identify false-positive test results. In one aspect, the secondary screen can use dihydrofolate reductase (DHFR) as a control.

In one embodiment, the protein of interest can be a heat shock protein (HSP), such as HSP70 or HSP90 or the host of Hsp90 cofactors. The protein stabilizer can inhibit a chaperonin from interacting with the other HSP molecules.

In one embodiment, the present invention includes a device, system, kit, or method as described herein suitable for studying protein conformation transformation. This can include one or more proteins of interest or functional portion thereof bound to a macroscopic substrate. The attachment of the protein of interest to the substrate can be performed via a linker between the substrate and the protein of interest. This linker can be used for extending the protein of interest away from the surface. The linker can include a polymer, aliphatic chain, antibody, chimeric construct, GST domain, histidine tag, SUMO tag, or combination thereof. Similarly, the chaperonin can also be bound to the substrate by a linker.

In one embodiment, the protein of interest can be linked through a chimeric attachment domain, such as a GST domain with histidine tag, SUMO tag with histidine tag, or any other chimeric protein tag. The use of a linker can provide optimal binding to the GroEL chaperonin because the binding site of the chaperonin is formed below the surface of the protein (e.g., it is in a large cavity).

In one embodiment, the methods described herein are performed without a fluorophore or other marker.

In one embodiment, the capture protein, target protein or chaperonin protein can be recombinant or otherwise modified from wild-type. However, wild-type proteins can be used as described herein. Particularly, the proteins can be altered with substitutions, deletions, or additions to the protein sequence in order to increase or decrease association kinetics. Altering the protein sequence can provide proteins with enhanced unfolding kinetics that can be used for determining stabilizers and/or destabilizers as described herein. The modified proteins can be used as described herein.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A method of studying protein conformation transformation, the method comprising:
providing a substrate surface bound with an immobilized protein, the immobilized protein being a protein of interest or functional portion thereof, the immobilized protein being bound to the substrate surface in a first conformation, the immobilized protein being capable of undergoing a conformation transformation to a second conformation under conformation transformation conditions while bound to the substrate surface;
providing a chaperonin composition having a chaperonin protein capable of binding to the immobilized protein during or after the immobilized protein undergoes the conformation transformation to the second conformation, wherein the chaperonin protein has weaker binding to the immobilized protein in the first conformation than during the conformation transformation or than in the second conformation;
inducing the conformation transformation of the immobilized protein from the first conformation to the second conformation before the immobilized protein is introduced into the chaperonin composition, the inducing of the conformation transformation comprising:
introducing the substrate surface bound with the immobilized protein to a denaturant solution so as to at least partially denature the protein of interest; and
removing the denaturant solution from the at least partially denatured immobilized protein before introducing the partially denatured immobilized protein to the chaperonin composition;
immersing the immobilized protein bound to the substrate surface into the chaperonin composition; and
detecting a change in binding of the chaperonin to the immobilized protein upon the immobilized protein undergoing the conformation transformation from the first conformation to the second conformation.

2. The method of claim 1, comprising:
introducing a potential protein stabilizer into the immobilized protein; and
determining whether the potential protein stabilizer is a protein stabilizer for the immobilized protein, wherein the potential protein stabilizer is a protein stabilizer when it stabilizes the immobilized protein and inhibits the conformation transformation from the first conformation to the second conformation.

3. The method of claim 2, comprising:
monitoring kinetics of a binding interaction between the chaperonin and the immobilized protein with and without presence of the potential protein stabilizer.

4. The method of claim 3, comprising:
determining the potential protein stabilizer to be a protein stabilizer for the protein at a desired pH value or range.

5. The method of claim 2, comprising: monitoring dynamic folding and/or unfolding of the immobilized protein with and without the potential protein stabilizer.

6. The method of claim 1, comprising: introducing a potential protein destabilizer into the immobilized protein; and
determining whether the potential protein destabilizer is a protein destabilizer for the immobilized protein, wherein the potential protein destabilizer is a protein destabilizer when it destabilizes the immobilized protein and induces the conformation transformation from the first conformation to the second conformation.

7. The method of claim 1, wherein the immobilized protein is selected from a bacterial toxin, viral protein, prion, or a protein involved in a protein folding disease.

8. The method of claim 1, wherein the immobilized protein conformation transformation is from the first conformation being a water soluble conformation to the second conformation being a membrane insertable conformation.

9. The method of claim 1, comprising:
performing the method with a biolayer interferometry (BLI) system.

10. The method of claim 1, comprising:
performing the method with a surface plasmon resonance (SPR) system.

11. The method of claim 2, comprising:
determining whether or not the potential protein stabilizer inhibits formation of an aggregation prone state of the immobilized protein during or after the conformation transformation.

12. The method of claim 1, comprising:
introducing a denaturant substance or denaturant condition to the immobilized protein so as to at least partially denature or fully denature the immobilized protein.

13. The method of claim 2, comprising:
introducing the immobilized protein to the potential protein stabilizer;
introducing the immobilized protein into a denaturant after the immobilized protein has been introduced to the potential protein stabilizer; and
removing the denaturant from the immobilized protein before being introduced to the chaperonin protein.

14. The method of claim 1, wherein the conformation transformation is induced by changing a condition selected from pH, presence of denaturant substance, amount of denaturant substance, temperature, or combination thereof.

15. The method of claim 2, wherein the conformation transformation is induced by changing a condition selected from pH, presence of denaturant substance, amount of denaturant substance, temperature, or combination thereof.

16. The method of claim 1, wherein the immobilized protein is immobilized to the substrate surface in a specific orientation.

17. The method of claim 1, wherein the immobilized protein is immobilized to the substrate surface via a linker.

18. The method of claim 1, comprising:
monitoring binding of the chaperonin to the immobilized protein; and
determining denaturation kinetics of the immobilized protein from the first conformation to the second conformation.

19. The method of claim 1, comprising determining a kinetic denaturation curve of the immobilized protein.

20. The method of claim 1, wherein the induction of the conformation transformation results in changing from the first conformation with less hydrophobic residues exposed to the second formation with more hydrophobic residues exposed.

21. A method of studying protein conformation transformation, the method comprising:
providing a substrate surface bound with an immobilized protein, the immobilized protein being a protein of interest or functional portion thereof, the immobilized protein being bound to the substrate surface in a first conformation, the immobilized protein being capable of undergoing a conformation transformation to a second conformation under conformation transformation conditions while bound to the substrate surface;
providing a chaperonin composition having a chaperonin protein capable of binding to the immobilized protein during or after the immobilized protein undergoes the conformation transformation to the second conformation, wherein the chaperonin protein has weaker binding to the immobilized protein in the first conformation than during the conformation transformation or than in the second conformation;
inducing the conformation transformation of the immobilized protein from the first conformation to the second conformation before the immobilized protein is introduced into the chaperonin composition by introducing a denaturant substance or a denaturant condition to the immobilized protein for a period of time and then removing the denaturant substance or denaturant condition from the immobilized protein before introducing the immobilized protein to the chaperonin composition;
immersing the immobilized protein bound to the substrate surface into the chaperonin composition; and
detecting a change in binding of the chaperonin to the immobilized protein upon the immobilized protein undergoing the conformation transformation from the first conformation to the second conformation.

22. A method of studying protein conformation transformation, the method comprising:
providing a substrate surface bound with an immobilized protein, the immobilized protein being a protein of interest or functional portion thereof, the immobilized protein being bound to the substrate surface in a first conformation, the immobilized protein being capable of undergoing a conformation transformation to a second conformation under conformation transformation conditions while bound to the substrate surface;
providing a chaperonin composition having a chaperonin protein capable of binding to the immobilized protein during or after the immobilized protein undergoes the conformation transformation to the second conformation, wherein the chaperonin protein has weaker binding to the immobilized protein in the first conformation than during the conformation transformation or than in the second conformation;
introducing the immobilized protein to a potential protein stabilizer;
inducing the conformation transformation of the immobilized protein from the first conformation to the second conformation before the immobilized protein is introduced into the chaperonin composition by introducing the immobilized protein into a denaturant after the immobilized protein has been introduced to the potential protein stabilizer;
removing the denaturant from the immobilized protein before being introduced to the chaperonin protein;
immersing the immobilized protein bound to the substrate surface into the chaperonin composition; and
detecting a change in binding of the chaperonin to the immobilized protein upon the immobilized protein undergoing the conformation transformation from the first conformation to the second conformation; and
determining whether the potential protein stabilizer is a protein stabilizer for the immobilized protein, wherein the potential protein stabilizer is a protein stabilizer when it stabilizes the immobilized protein and inhibits the conformation transformation from the first conformation to the second conformation.

* * * * *